United States Patent
Coleman et al.

(10) Patent No.: US 6,882,419 B2
(45) Date of Patent: Apr. 19, 2005

(54) SYSTEM FOR IMPROVED BIOLOGICAL NUTRIENT REMOVAL

(76) Inventors: Thomas E. Coleman, 419 29th Place N., Yakima, WA (US) 98902; James E. Bruya, 12427 14th Ave. SW., Seattle, WA (US) 98146

(*) Notice: Subject to any disclaimer, the term of this patent is extended or adjusted under 35 U.S.C. 154(b) by 254 days.

(21) Appl. No.: 10/284,382

(22) Filed: Oct. 31, 2002

(65) Prior Publication Data

US 2003/0142301 A1 Jul. 31, 2003

Related U.S. Application Data

(60) Provisional application No. 60/330,829, filed on Oct. 31, 2001.

(51) Int. Cl.$^7$ .................................................. G01J 3/44
(52) U.S. Cl. ...................................... 356/301; 436/110
(58) Field of Search ................................ 356/301, 302, 356/303, 319; 436/106, 107

(56) References Cited

U.S. PATENT DOCUMENTS 6,040,906 A * 3/2000 Harhay ........................ 356/301
6,051,436 A * 4/2000 Reagen et al. ............... 436/106

OTHER PUBLICATIONS

Xi et al, Determination of low concentrations of the azo–dye complex of nitrite in fresh water and seawater using surface–enhanced resonance Raman spectroscopy (SERRS), 1992, Applied Spectroscopy, v 46(5), pp 819–826.*

* cited by examiner

Primary Examiner—Layla Lauchman
(74) Attorney, Agent, or Firm—Birch, Stewart, Kolasch & Birch, LLP

(57) ABSTRACT

A method is provided for the determination of $NO_2^-$ and/or $NO_3^-$ in water by subjecting the water sample to ultraviolet resonance Raman spectroscopy within the range of wavelengths of 200–240 nm, and determining the presence of $NO_2^-$ and/or $NO_3^-$ based on the Raman spectral measurement. The method has particularly applicability to the determination of such ions in wastewater, such as in activated sludge washwater treatment reactors. The method may also be employed with advantage in the control of processes involving the removal of ammonium ions upon reaction with oxygen.

20 Claims, 26 Drawing Sheets

SYSTEM FOR IMPROVED BIOLOGICAL NUTRIENT REMOVAL

This application claims priority on provisional Application No. 60/330,829 filed on Oct. 31, 2001, the entire contents of which are hereby incorporated by reference.

The invention was made with Government support under Small Business Innovation Research Contract No. 68-D-00-234 awarded by the Environmental Protection Agency.

BACKGROUND OF THE INVENTION

The present invention is directed to the use of ultraviolet resonance Raman (UVRR) spectroscopy and membrane filtration techniques for the development of an on-line monitoring and process control system that will improve the reliability and performance of biological nutrient removal (BNR) wastewater treatment plants (WWTPs). This monitoring system enables real time in situ measurement of nitrate and nitrite in BNR activated sludge reactors without the need for reagent additions or complex calibration procedures. Real time on-line monitoring of these parameters can provide input to a process control system used to optimize performance of treatment systems designed for low effluent concentrations of both nitrogen and phosphorus. An additional benefit will be the reduction of energy consumption for process aeration.

This system can be readily applied to the monitoring and control of simultaneous nitrification and denitrification (SNdN), and would be particularly applicable to the control of the relatively new membrane bioreactor (MBR) treatment processes which are rapidly gaining interest for BNR and water reclamation treatment facilities.

The generally accepted energy yielding two-step oxidation of ammonia to nitrate is as follows. (Randall et al., 1992):

*Nitrosomonas*

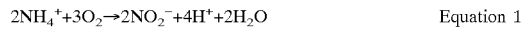
$$2NH_4^+ + 3O_2 \rightarrow 2NO_2^- + 4H^+ + 2H_2O \qquad \text{Equation 1}$$

*Nitrobacter*

$$2NO_2^- + O_2 \rightarrow 2NO_3^- \qquad \text{Equation 2}$$

The total reaction is

$$NH_4^+ + 2O_2 \rightarrow NO_3^- + 2H^+ + H_2O \qquad \text{Equation 3}$$

The total reaction shows that 4.57 g $O_2$ is required per g-$NH_4^+$—N oxidized, but when the nitrogen used for cell syntheses is included the oxygen requirement is 4.3 g $O_2$/g-$NH_4^+$—N oxidized to nitrate (Randall et al. 1992). Temperature, dissolved oxygen (DO) concentration, and ammonia nitrogen concentration all affect nitrification rates. Nitrification kinetics is normally based on ammonia concentrations since nitrite is oxidized rapidly under fully aerobic conditions. The actual growth rate of nitrifiers ($\mu_N$) can be expressed as a function of ammonia and DO by a Monod kinetic equation:

$$\mu_N = \mu_{Nmax} \times [(NH_4^+ - N)/(K_N + NH_4^+ - N)] \times [(DO)/(K_o + DO)] \qquad \text{Equation 4}$$

At very low DO levels the term [(DO)/($K_o$+DO)] approaches zero and nitrification will no longer occur. Under long periods of very low DO conditions the nitrifiers will be lost from the system.

Nitrate reduction in wastewater systems occurs through assimilation and denitrification. In assimilatory nitrate reduction, nitrate is reduced to ammonia and assimilated for cell synthesis. In denitrification bacteria use nitrate as an electron acceptor in the absence of oxygen to oxidize an organic or inorganic electron donor. Nitrate is reduced to nitrite, to nitric oxide, to nitrous oxide, and to nitrogen in a four-step process (Payne et al, 1981):

$$NO_3^- \rightarrow NO_2^- \rightarrow NO \rightarrow N_2O \rightarrow N_2 \qquad \text{Equation 5}$$

The rate of denitrification ($R_{DN}$) is dependent on temperature and DO concentration, where K is the temperature correction coefficient which is commonly assumed to be 1.09.

$$R_{DN(T)} = R_{DN(20)} \times K^{(T-20)} \times (1-DO) \qquad \text{Equation 6}$$

Equation 6 shows that the rate of denitrification decreases linearly from 0 to 1 mg/l of DO. At DO levels of 1 mg/l and above the rate of denitrification becomes negligible. From equations 4 and 6, it is apparent that in order to have conditions which support SNdN it is necessary to maintain the DO concentration within a very narrow range.

Aeration control methods based on a DO measurement feedback loop have proven to be inadequate to achieve reliable and consistent SNdN operating conditions. The problems with DO measurement alone are twofold. The first problem is that DO instrumentation has historically been unable to provide the necessary accuracy at the very low DO levels required to achieve SNdN (typically in the range of 0 to 0.3 mg/l). A second and more fundamental problem is that the DO measurement alone is not sufficient to define the nitrification and denitrification metabolic conditions within the reactor. Nitrification and denitrification rates are a function of DO, temperature, pH, solids retention time (SRT), microbial population dynamics, and other factors. For example, one system under a given set of conditions may lose nitrification at a DO level of 0.3 mg/L while another system may continue to nitrify when the measured DO level in the bulk solution is very near 0 mg/L.

Other instrumentation and control methods have been applied to attempt control of SNdN process reactors including nicotinamide adenine dinucleotide (NADH) sensors, oxidation reduction potential (ORP) electrodes, and on-line nitrate analyzers. Each of these methods has significant limitations in the application to SNdN control due to cost and/or performance issues.

The performance and cost effectiveness of the measurement and control method proposed here will greatly exceed those of the currently available methods for SNdN control. Our proposed method will use UVRR for direct simultaneous measurement of both nitrate and nitrite. The control algorithm will be based on the calculated ratio of nitrite to nitrate.

Recent research using laboratory bench scale reactors (Kuai and Verstraete, 1998) has demonstrated that the nitrite oxidizers responsible for conversion of nitrite to nitrate are strongly inhibited by low DO concentrations. In this work $NO_2^-/(NO_2^- + NO_3^-)$ ratios were found to be in the range of 0.9 to 1.0 under oxygen limiting conditions. Under fully aerobic conditions nitrite concentrations are typically very low and the corresponding ratio of $NO_2^-/(NO_2^- + NO_3^-)$ ratio will also be very low (<0.1).

Other researchers have also observed that at very low DO concentrations a "Nitrite Shunt" may be occurring (O'Neill and Huren, 1995), in which nitrite is produced from nitrification without nitrate formation due to inhibition of the nitrite-oxidizing bacteria by the low DO concentration. The removal of ammonia under these conditions is assumed to occur in a two step process as follows:

$$2NH_4^+ + 3O_2 \rightarrow 2NO_2^- + 4H^+ + 2H_2O \quad \text{Equation 7}$$

$$2NH_4^+ + 2NO_2^- \rightarrow 2N_2 + 4H_2O \quad \text{Equation 8}$$

With the overall reaction being:

$$4NH_4^+ + 3O_2 \rightarrow 2N_2 + 6H_2O + 4H^+ \quad \text{Equation 9}$$

Based on the above stoichiometry, the removal of ammonium nitrogen via the nitrite shunt pathway results in a 63% energy savings versus conventional nitrification processes (Kuai and Verstraete, 1998) and nearly 40% versus conventional nitrification-denitrification processes.

Regardless of whether SNdN is a result of the formation of anoxic regions within an otherwise aerobic environment due to incomplete mixing, a result of diffusional limitations on the oxygen transfer into the floc (causing an anoxic region within the floc itself), a distinct biological phenomenon (such as the "nitrite shunt" pathway), or a combination of these factors, the measurement and control system that we propose is ideally suited to maintaining conditions in a reactor to maximize the potential for reliably and efficiently achieving SNdN. The algorithm for aeration system control to achieve SNdN using our system would utilize high and low setpoints for the ratio of nitrite to nitrate with the objective of maintaining DO levels as low as possible without losing nitrification. Where possible, designers and operators of BNR treatment facilities may elect to establish setpoint values which maximize the potential for promoting the nitrite shunt pathway to achieve additional energy savings. The widespread implementation of a monitoring and control system with these capabilities can be expected to lead to significant progress in the understanding of SNdN metabolic pathways and practical application methods.

Raman spectroscopy is the measurement of the wavelength and intensity of inelastically scattered light from molecules. The Raman scattered light occurs at wavelengths that are shifted from the incident light by the energies of molecular vibrations. Light photons which are shifted to a lower energy (longer wavelength) are said to be Stokes shifted while a shift to a higher energy (shorter wavelength) is termed an anti-Stokes shift. Elastic photon collisions result in Rayleigh scattering, where the energy of the photon is the same before and after the collision. In Rayleigh scattering, only the photon's direction of travel has changed.

Raman spectroscopy was first discovered in 1928 by C. V. Raman (Raman and Krishnan, 1928), but in recent years has been revolutionized by several new technological developments, resulting in enormous increases in Raman signal detection capabilities, lower instrumentation costs, and relatively compact equipment that permits mobile, on-site measurements. Raman spectroscopy, compared to competing techniques for chemical identification, has minimal requirements for sample preparation and requires no reagent additions. Raman spectroscopy can readily be used in aqueous systems since the water molecule has very weak Raman activity. These factors have led to a growing interest in Raman spectroscopy in industry for chemical identification and for on-line monitoring and control. This rapidly emerging technology offers significant opportunities for development of applications in the monitoring and control of wastewater treatment processes.

The intensities of Raman shift spectral bands are only a very small percentage of the excitation light source which makes their detection and measurement experimentally difficult. Nitrate and nitrite have Raman shift lines due the symmetrical N—O stretch vibrational mode at 1044 cm$^{-1}$ and 1325 cm$^{-1}$ respectively (Laane and Ohlsen, 1980) which represent the reduction of energy of the observed line from the incident light wave number where both are given in cm$^{-1}$.

The intensity of a Raman shift line is proportional to the fourth power of the excitation source frequency. Therefore, using a light source in the red region produces relatively low intensity lines for the symmetrical N—O vibration Raman shifts. A shorter wavelength (higher frequency) excitation source in the green or blue region can be obtained by using, for example, a Nd:YAG laser at 532 nm. The higher excitation frequency will increase the intensity of the Raman shift line, however the problem with doing this is that many organic compounds including many of those found in wastewater, exhibit strong fluorescence of blue and green wavelengths making it impossible to get good signal to noise Raman spectra.

Going to even shorter wavelengths into the UV and deep UV region will further increase the intensity of the Raman shifts due to the effect of the higher frequency excitation. It also avoids the potential interference from fluorescence since condensed phase species typically show no fluorescence below 260 nm (Asher, Munro, and Chu 1997, Asher and Johnson 1985). Even more significantly, since nitrate and nitrite are both strong absorbers of UV light at around 200 to 220 nm, it becomes possible to take advantage of the resonance Raman effect. Resonance Raman scattering requires excitation within an electronic absorption band and results in a large increase of scattering. The resonance Raman scattering can be up to 10$^8$ times that of "normal" Raman scattering. (Asher 1993, and Dudik, et al., 1985).

Wastewater treatment plant managers and operators are now facing increasingly stringent regulations, more demanding reporting requirements, pressure to hold down costs, and requirements to improve the treatment performance, particularly in the area of nutrient removal. Improved on-line monitoring and automation of process controls are critical in meeting these challenges. According to the Water Environment Research Foundation (WERF), poor sensor performance and high maintenance costs have been considered the major stumbling blocks to improved automation. (Water Environment Research Foundation, 1998)

Nutrient removal is a significant concern for municipal discharges in many areas of the United States and around the world. The most common, widely accepted and economical approach to accomplish nitrogen removal involves biological nitrification and denitrification. Nitrogen enters municipal wastewater treatment plants in the form of organic nitrogen and ammonia, and during nitrification, the nitrogen is oxidized by autotrophic bacteria to nitrite and nitrate nitrogen. During biological denitrification, biological reactors are operated without oxygen addition, so that the bacteria use nitrate as an electron acceptor for their respiration. Various designs are used, and one of the most common approaches employs an anoxic tank (anoxic meaning bacteria respiration with nitrate in the absence of oxygen) ahead of aeration where recycled nitrate is contacted with influent wastewater to promote nitrate reduction to nitrogen gas.

Where phosphorus removal is also required, the historical approach and one that is still used at most municipal WWTPs is to add aluminum or iron salts to the wastewater treatment process. This method has many disadvantages which include: 1) chemical cost; 2) increased sludge production and difficulty in sludge dewatering; 3) consumption of additional energy for chemical production and transportation to the site; and 4) production of a greater quantity of waste for ultimate disposal. An alternative approach that has received increased acceptance in the last fifteen years is the use of combined biological nitrogen and phosphorus removal processes.

Biological phosphorus removal designs are commonly coupled with nitrogen removal designs by adding an anaerobic contact zone before the first anoxic zone, as shown in FIG. 1, to promote the growth of phosphate accumulating bacteria. The flow scheme depicted here is for the Bardenpho BNR process.

The major limitation of the above biological nutrient removal systems, and other similar BNR designs, is the inability to consistently achieve effluent phosphorus concentrations as low as is necessary to meet most discharge permit limitations (usually less than or equal to 1.0 mg/L as P). In some cases chemicals are added for polishing to lower the phosphorus concentration from that achieved by the biological process, but where this would be necessary it often discourages designers from using biological phosphorous removal in the first place. (Daigger, 1991)

The treatment efficiency limitations of current biological phosphorus removal processes are due to two causes. The first cause of lower phosphorus removal is a low concentration of influent soluble biochemical oxygen demand (BOD). Sufficient BOD is needed to produce the necessary acetate to form polyhydroxy-butyrate (PHB) which is needed in the aerobic zone for phosphorus uptake. This problem is overcome by providing supplemental acetate or sugar to the anaerobic zone. In some cases primary clarifier solids are fermented to provide this necessary acetate.

The second cause of lower phosphorus removal is the occurrence of extended anaerobic contact time where acetate is not available. In this case phosphorus is released without concurrent acetate uptake and PHB formation, making insufficient electron donor present during aeration to provide energy for uptake and formation of polyphosphates from all of the released phosphorus.

Stephens and Stensel (1998) reported that only 40 to 60% of the phosphorus released during anaerobic contacting following nitrate depletion, and without acetate, was taken up during aeration in a sequence batch reactor process during laboratory experiments. Barnard (1984) had hypothesized this phenomena earlier and termed it "secondary phosphorus release", but only recently has experimental data been presented to indicate its existence and negative impact on biological phosphorus removal.

The potential for "secondary phosphorus release" is great in BNR systems since full-scale facilities are not normally operated at their future maximum expected design loadings. This means that the anoxic zones are larger than needed for much of the operation which will encourage periods of anaerobic conditions (lack of nitrate and oxygen) thus promoting secondary phosphorus release. The problem may also be related to diurnal or seasonal load changes such that periods of excess anoxic zone capacity exist at different times resulting in periodic secondary phosphorus release. Since the anoxic tank capacity must be available to meet higher loads, a monitoring and control system is needed that can respond to changing plant loads and prevent secondary phosphorus release. The key technological development needed to implement a control strategy based on these principles is a cost effective and reliable sensor system capable of monitoring nitrate and nitrite down to 1 mg/L or less.

There is also a great deal of interest currently in developing process designs and control strategies capable of achieving simultaneous nitrification and denitrification. By maintaining very long mean cell residence times, sometimes through the use of immobilization techniques or membrane separation processes, and close control over dissolved oxygen levels, it is possible to achieve ammonia oxidation to nitrite with the nitrite being reduced to nitrogen gas in the same reactor. In these systems the dissolved oxygen (DO) levels must be maintained at very close to zero making it impossible to use a DO feedback loop for control of the aeration system. The ability to obtain real time in situ measurements of nitrate and nitrite in the reactors would significantly enhance the potential application of this type of process. The ability to achieve nitrification and denitrification in one reactor could be a particularly attractive option for upgrading existing treatment facilities to meet more stringent total nitrogen effluent limits.

With increased emphasis on the reuse of treated effluent for land application or groundwater recharge, it becomes necessary to optimize total nitrogen removal in both new and existing facilities. The application of the online nitrate/nitrite monitoring and control system to a multistage nitrification/denitrification facility would be similar to that described above for control of secondary phosphorous release, except that it would be used to adjust the anoxic and aerobic zone operating conditions under varying loading conditions to maximize total nitrogen removal.

Nitrate analyzers which are based on dual beam UV absorption spectroscopy are offered by several manufacturers. These analyzers measure absorption of the samples at two different wavelengths, typically 210 nm and 250 nm. The absorption at 210 nm can be related to the concentration of $NO_x$ ($NO_2^-$ plus $NO_3^-$) and the absorption at 250 nm is used to correct for the presence of organic compounds which also exhibit some absorption at 210 nm. This method has two significant drawbacks. First, it cannot differentiate nitrate from nitrite and is, therefore, not suitable for determination of the nitrite to nitrate ratio as is necessary to maintain low DO operating conditions. The second major drawback is the potential for interference from organic compounds present in the wastewater requiring that the instrument be calibrated based on the individual wastewater characteristics at each treatment plant installation.

Other methods exist for nitrate and nitrite analysis including automated analyzers using reagent based spectrophotometric methods and adaptations of these reagent based methods using flow injection analysis (FIA). These methods can be relatively expensive, require regular replacement of reagents, frequent calibration and periodic cleaning and/or replacement of pumps and tubing. For application to the problem of on-line monitoring and control, these methods also have limitations with respect to the length of time required to collect a sample and make a measurement that could be used as an input to a real time process control system.

U.S. Pat. No. 5,246,868 discloses the use of infrared emissions to determine the presence of excited molecules in samples of interest. Laser energy may be employed; however, the patent focuses on gas phase samples. Determinations based on waste water are taught.

U.S. Pat. No. 5,480,562 teaches the use of a laser to detect the presence of organisms in water by optical scanning. The scanned information may be used to assist in the purification of the water sample.

U.S. Pat. No. 5,528,363 is directed to an integrated device for detection and identification of an entity in a sample. The assaying of groups by laser in a liquid sample is disclosed, such as nitrate, phenol, chromium, various metals, chlorides, borates, phosphates, ammonium, etc.

U.S. Pat. No. 5,030,419 is directed to a wastewater pollutant sensor where the presence of chemicals on the emitting surface of the surface-derivatized photoluminescent semiconductor alters the characteristics of radiation-emitted from the surface. The degree of alteration will indicate the presence of chemicals in the environment. The patent provides for the use of laser energy to irradiate the semiconductor.

DETAILED DESCRIPTION OF THE INVENTION

Figure 1:
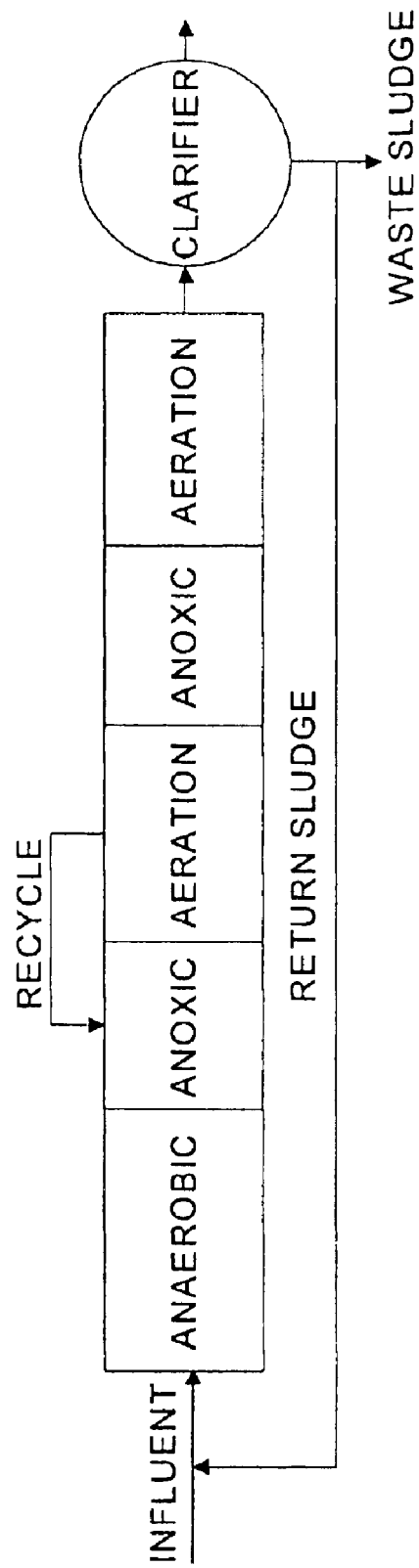
FIG. 1 is a schematic showing a typical combined biological phosphorus and nitrogen removal process.

Various experiments were conducted to determine the effectiveness of determination of nitrite and nitrate ions in aqueous solution by means of UV resonance Raman spectral measurement.

Standards for nitrate and nitrite were prepared from 0.1 to 50 ppm (as N) in increments as follows: 0.1, 0.2, 0.5, 1.0, 2.0, 5.0, 10, 20, 30, 40, 50 ppm. These initial nitrate and nitrite standards were prepared from a 1000 ppm and a 0.1 M reagent grade standard solutions respectively. Both of the standard stock solutions were traceable to NIST primary standard sources. Reagent Grade Type II water was used in the preparation of these standards.

A solution sample representative of the soluble components of an activated sludge process reactor was prepared. The sample was obtained from the Grand Coulee, WA municipal wastewater treatment plant (design capacity 0.30 MGD) which uses a cyclic aerobic/anoxic process operating mode. A sample of mixed liquor was drawn from the aeration basin just at the end of an anoxic period when all of the nitrate and nitrite have been depleted. The sample was immediately filtered, through a 0.45 $\mu$m membrane filter to obtain a solution containing only the soluble components of the mixed liquor. This sample was subsequently used as the stock solution for the preparation of the nitrate and nitrite standards in the same increments as the pure water standards as describe above. The wastewater standards were prepared in the same manner except that the filtered wastewater solution was used instead of reagent grade water to make the necessary dilutions.

Three additional wastewater sample solutions were obtained in a similar manner. One of these samples was again from the Grand Coulee, WA WWTP. The second sample was from the Bingen, WA WWTP (design capacity 0.80 MGD) which utilizes a cyclic aerobic/anoxic process operating mode very similar to Grand Coulee. Both of these samples were fully depleted of nitrate and nitrite at the time they were collected and filtered. The third sample was obtained from the Zillah, WA WWTP (design capacity 0.31 MGD). The Zillah plant was experiencing a mild process upset at the time with a more turbid effluent than normal when the sample was collected. The upset conditions had begun about two weeks previously. Because of the timing of the sample collection, it was not possible to collect a sample which was fully depleted of nitrate and nitrite. In lieu of reaching the depletion end point, the filtered sample was analyzed for nitrate plus nitrite (often referred to as $NO_x$) using the Hach cadmium reduction method. This method usually provides an acceptable approximation for nitrate since nitrite concentrations are typically much lower than the nitrate concentrations. The result of this analysis was 4 mg/L as N. As discussed below, the results of the Raman spectral analysis of this sample proved to be both surprising and an interesting example of the potential capabilities of the application of this analytical method to wastewater treatment process monitoring and control.

For the excitation of nitrate and nitrite solutions for UV resonance Raman spectral measurements, either 204 nm obtained by anti-Stokes Raman shifting the third harmonic of a Coherent Inc. Infinity Nd:YAG laser in $H_2$ (Lednev, et al, 1999), or 229 nm a "Blue Fred" Coherent Inc. continuous wave (CW) intracavity frequency-doubled argon ion laser (Asher, et al., 1993) was used. The Raman scattered light was collected in a ~135° back-scattering geometry and dispersed by a Spex double or single monochromator. An intensified CCD detector (Princeton Instrument Co.) was used for detection. Winspec software was used to accumulate the spectra, whereas Grams software was used for the spectra treatment and analysis. Typically, an accumulation time of 10 minutes was used to record the spectra with high signal to noise ratios. However, accumulation times as low as one minute could be used to obtain the Raman spectra of nitrate and nitrite samples depending on the signal to noise requirements for a specific application. The samples were measured in a free-surface flowing stream (Lednev, et al, 1999). The intensity of the Raman spectra were adjusted using both internal and external Raman standards. The 1379 $cm^{-1}$ Teflon band was used as an external Raman intensity standard. The Raman spectrum of Teflon was recorded before or immediately after acquisition of the sample spectrum. The 1640 $cm^{-1}$ water band was used as the internal Raman intensity standard.

UV-vis absorption spectra covering a wavelength range from 200 nm to 400 nm were obtained with a Perkin-Elmer Lambda 9 spectrophotometer in a 0.5 cm cuvette.

Figure 2:
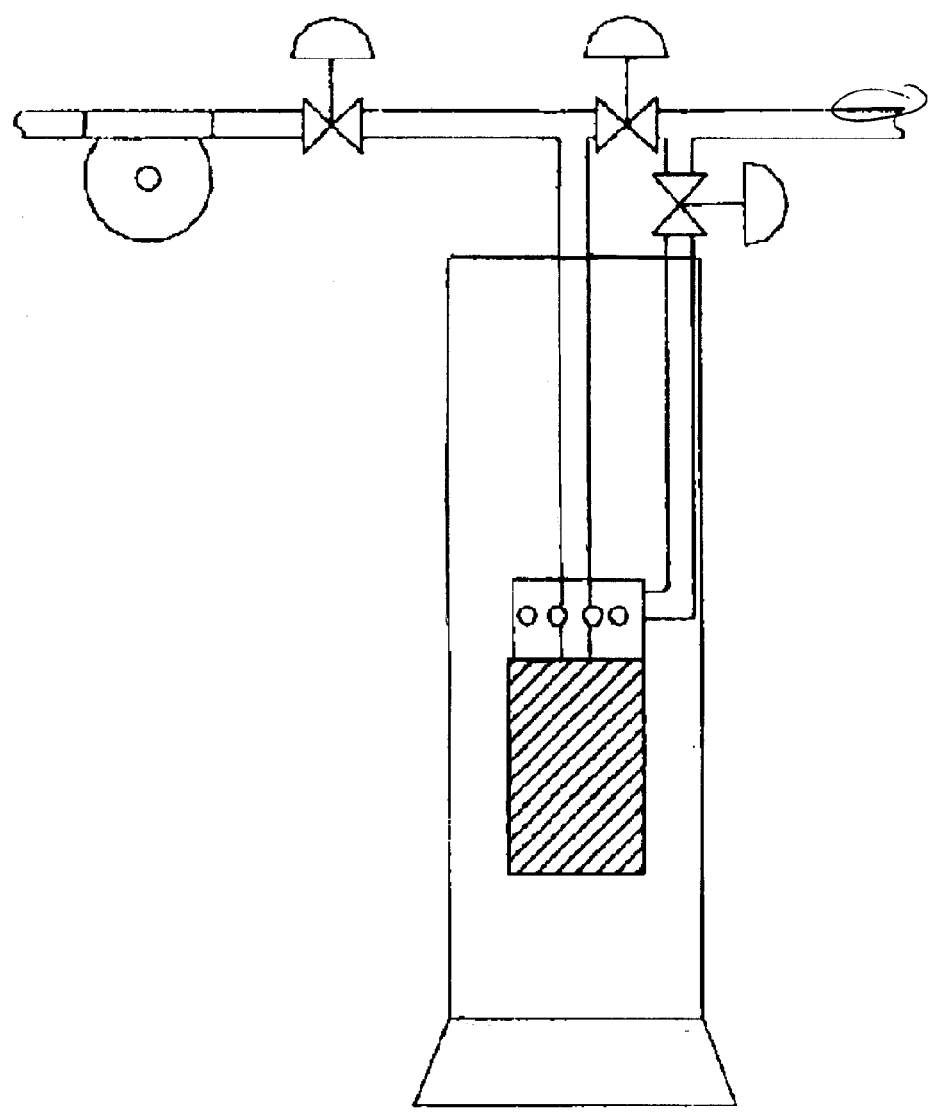
FIG. 2 is a schematic diagram of the cross-flow in situ membrane filtration assembly.

Two different types of in situ membrane filtration assemblies were fabricated for bench scale testing using activated sludge mixed liquor from municipal wastewater treatment plants. The first assembly was designed for cross-flow filtration and was constructed of 4-inch diameter clear acrylic tubing. A schematic diagram showing the configuration of this assembly is shown in FIG. 2. The cross flow hydraulic conditions and exchange of liquid with the reactor tank contents was accomplished using an air lift pump assembly located just above the filtration membrane cartridge. A Wallace & Tiernan Encore 700 44 Series diaphragm metering pump was used to draw liquid through the membrane filtration cartridge. The assembly also included the necessary piping and valves to backflush the membrane filtration cartridge with compressed air.

Figure 3:
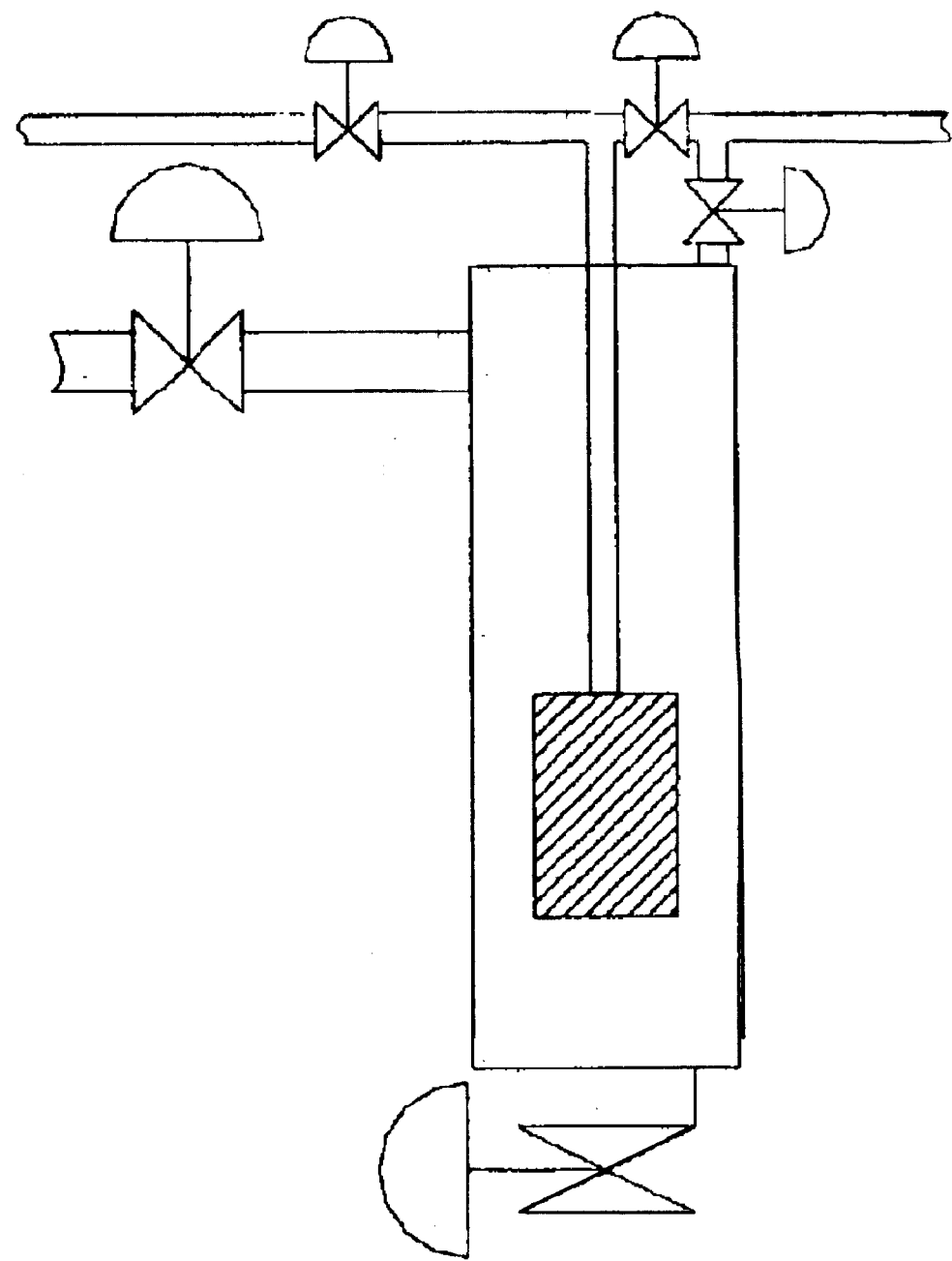
FIG. 3 is a schematic diagram of pressurized in situ membrane filtration assembly.

The second filtration assembly was constructed of 3-inch diameter clear PVC piping material and was designed as a pressurized chamber as shown schematically in FIG. 3. The chamber was pressurized with compressed air to force liquid through the membrane filtration cartridge. Backflushing was also accomplished by forcing compressed air back through the membrane.

During the backflush cycle the sampling chamber is opened to atmosphere on the top and to the reactor tank contents on the bottom. In this mode the chamber becomes an air lift pump to affect an exchange of liquid with the activated sludge reactor.

Commercially available membrane filtration cartridges tested using each of these in situ filtration assemblies included a Whatman PolyCap AS 0.45 $\mu$m cartridge and a 1.0 $\mu$m pleated polyester filter cartridge (Harnsco No. 801-1). Preliminary testing was also conducted using pleated cellulose membrane cartridges ranging from 2.0 $\mu$m to 20 $\mu$m. The PolyCap AS consists of an absolute nylon membrane with a glass fiber pre-filter. The polyethylene capsule housing was removed from the PolyCap AS to expose the membrane surfaces directly to the mixed liquor in the in situ assemblies. The other cartridges were mounted in the filtration assemblies using a compression fitting adapter that was fabricated from PVC for this purpose.

Figure 4:
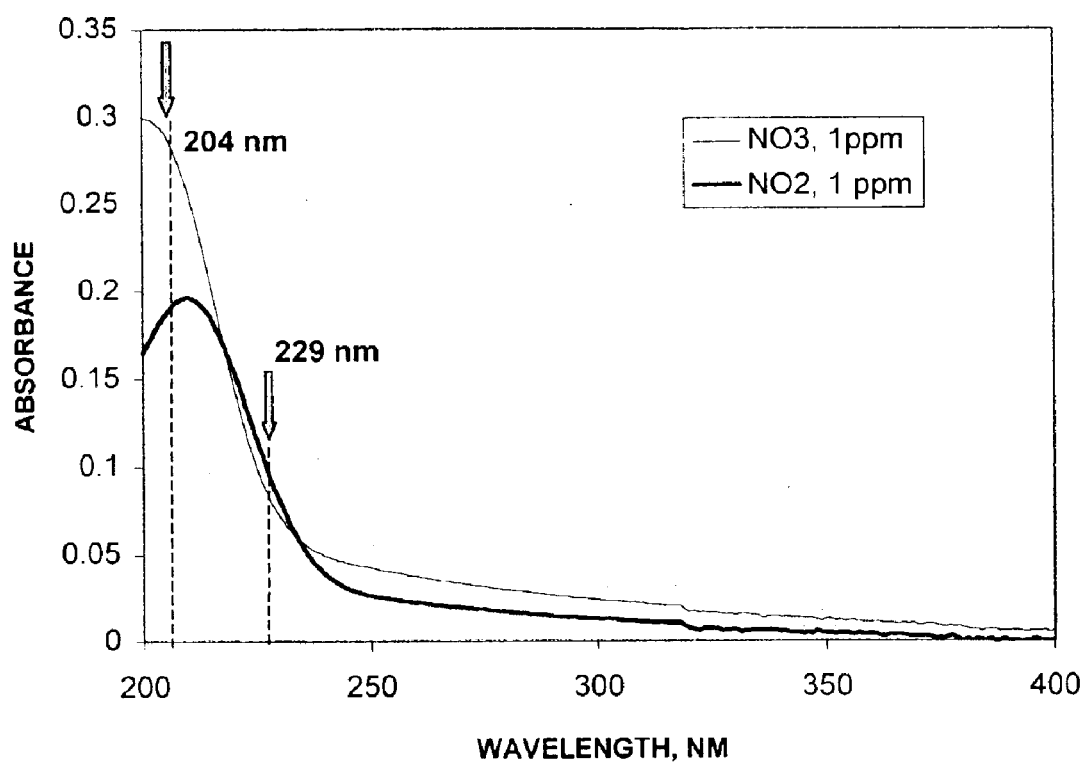
FIG. 4 is a UV-vis absorption spectra of nitrite and nitrate in pure water.

Absorption spectra of nitrate and nitrite in the deep UV are presented in FIG. 4. The absorption spectrum of $NO_3^-$ is slightly blue-shifted (maximum near 200 nm) as compared to the spectrum of $NO_2^-$ (maximum near 210 nm). In addition, the $NO_3^-$ molar absorption was found to be $8.4 \times 10^3$ l/(M×cm) which is about 50% higher than that of $NO_2^-$ ($5.6 \times 10^3$ l/(M×cm)).

Figure 5:
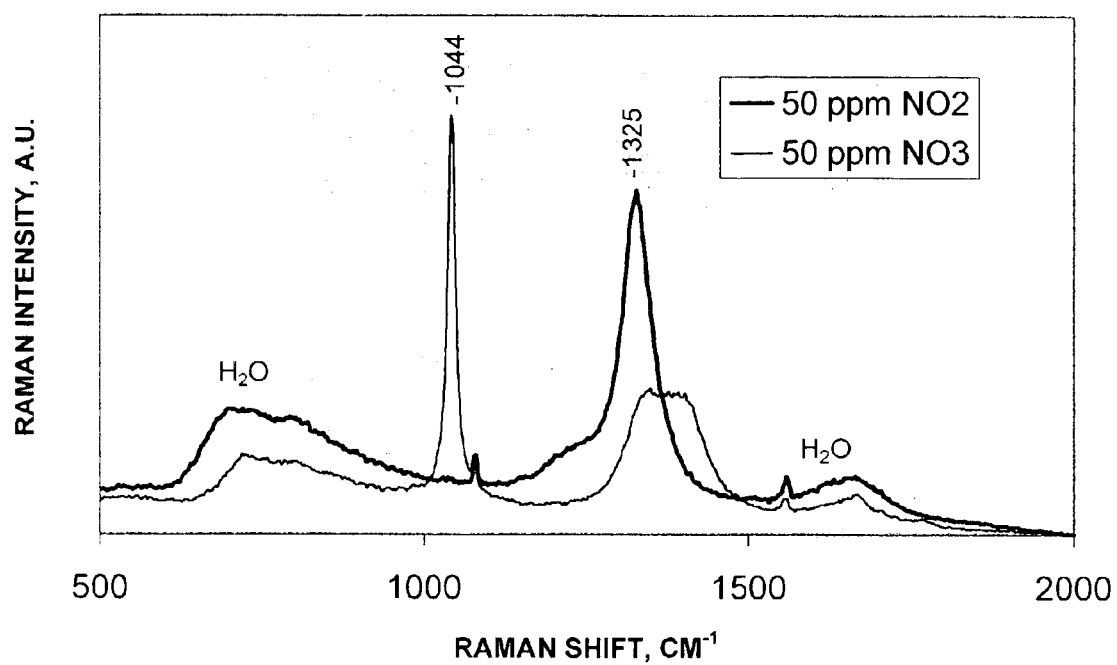
FIG. 5 is depicts UV resonance Raman spectra of 50 ppm solutions of $NO_2$ and $NO_3$.

For UV resonance Raman spectroscopy to be used to detect low concentrations of $NO_2^-$ and $NO_3^-$ in wastewater treatment plant BNR reactors the following criteria must be met:

1. That the Raman spectra of $NO_2^-/NO_3^-$ can be spectrally distinguished;
2. That these compounds can be detected at less than 1.0 ppm concentrations;
3. That the UV resonance Raman spectra of $NO_2^-/NO_3^-$ in filtered activated sludge process streams also have a less than 1.0 ppm detection limit;

UV resonance Raman spectra of nitrate and nitrite in pure water are presented on FIG. 5. The main bands in the spectra correspond to N—O stretch vibrations at 1044 $cm^{-1}$ for $NO_3^-$ and near 1325 $cm^{-1}$ for $NO_2^-$. Some medium intensity bands in the spectrum of $NO_3^-$ are also observed between 1300–1500 $cm^{-1}$.

Nitrate and nitrite are spectrally very different and can be easily distinguished in a mixture. There is a partial overlap of the 1325 $cm^{-1}$ $NO_2^-$ band with $NO_3^-$ bands. However, the contributions from nitrate in that spectral interval can be numerically removed to obtain the pure nitrite Raman signal by using the $NO_3^-$ 1044 $cm^{-1}$ band as an internal standard.

Nitrate and nitrite bands are spectrally separated from the solvent (water) bands at ~750 and 1640 $cm^{-1}$. Therefore water bands as an internal standard can be used.

Figure 6:
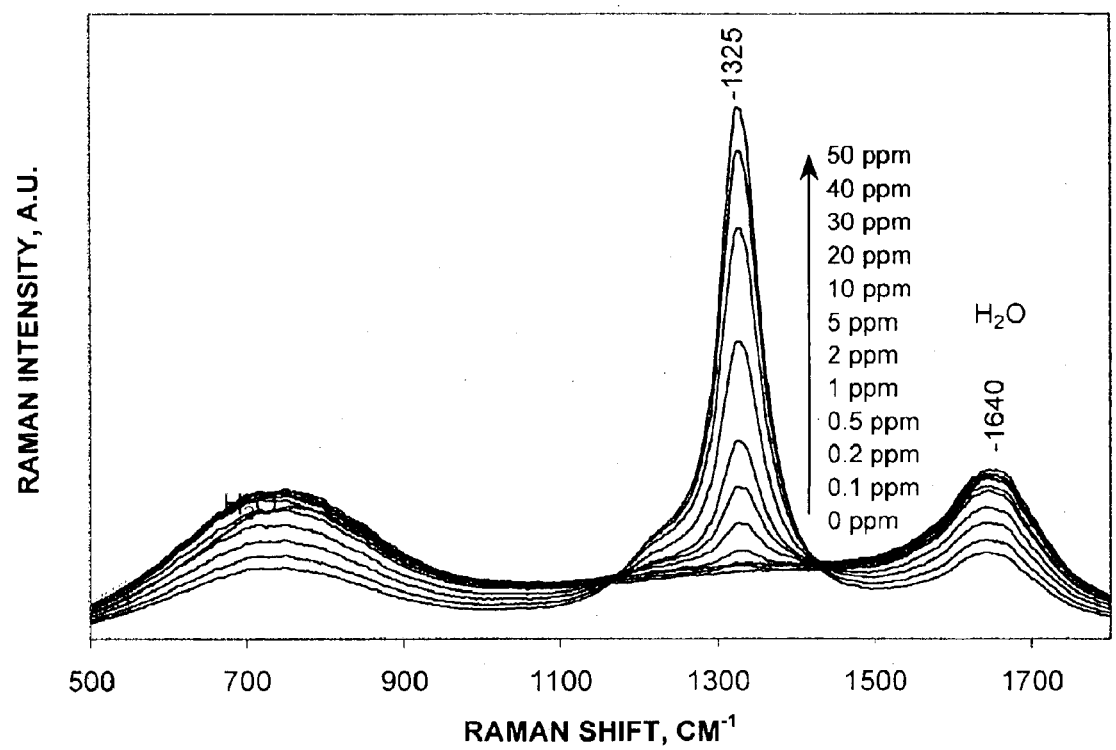
FIG. 6 depicts UV resonance Raman spectra of $NO_2$ in pure water.
Figure 6A:
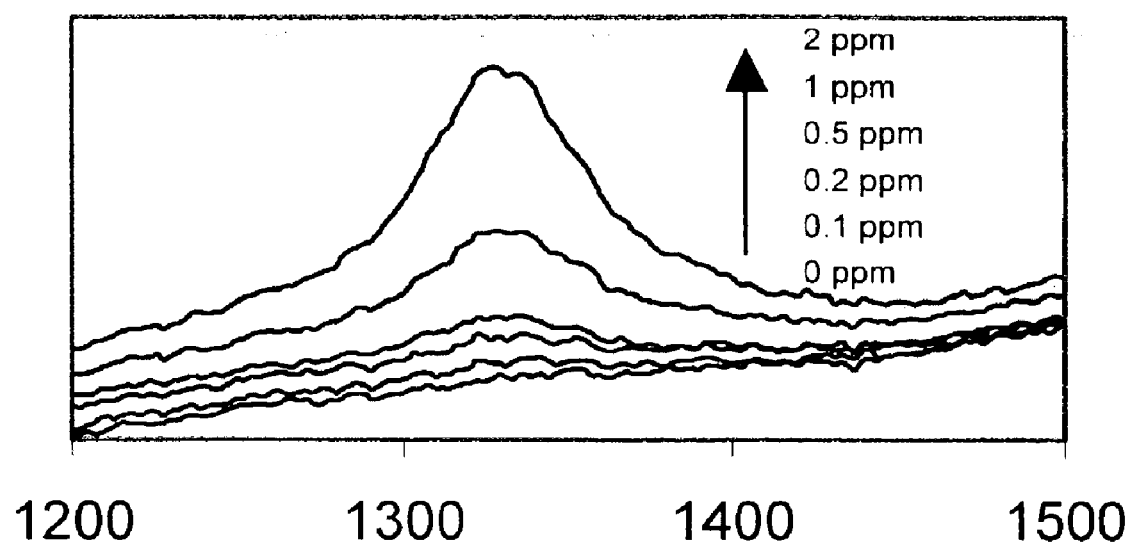
FIG. 6A is an enlarge view of a portion of FIG. 6.
Figure 7:
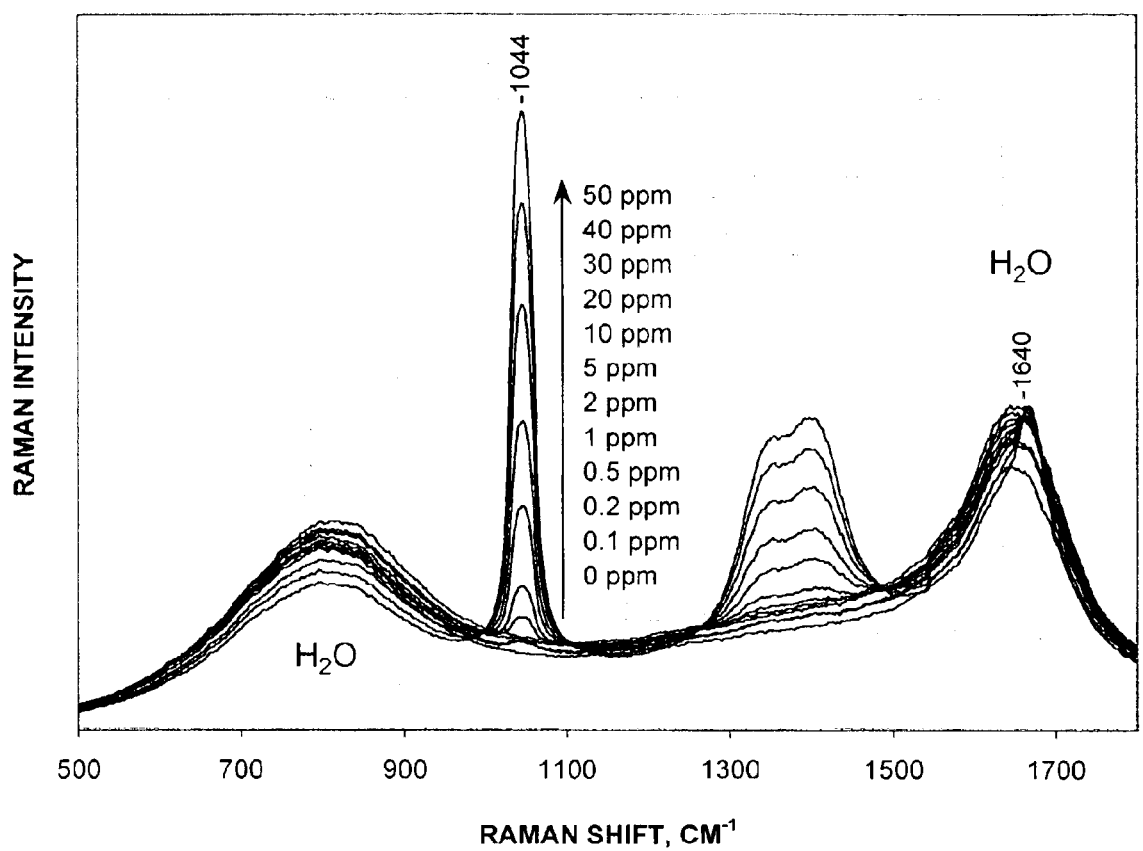
FIG. 7 depicts UV resonance Raman spectra of $NO_3$ in pure water.
Figure 7A:
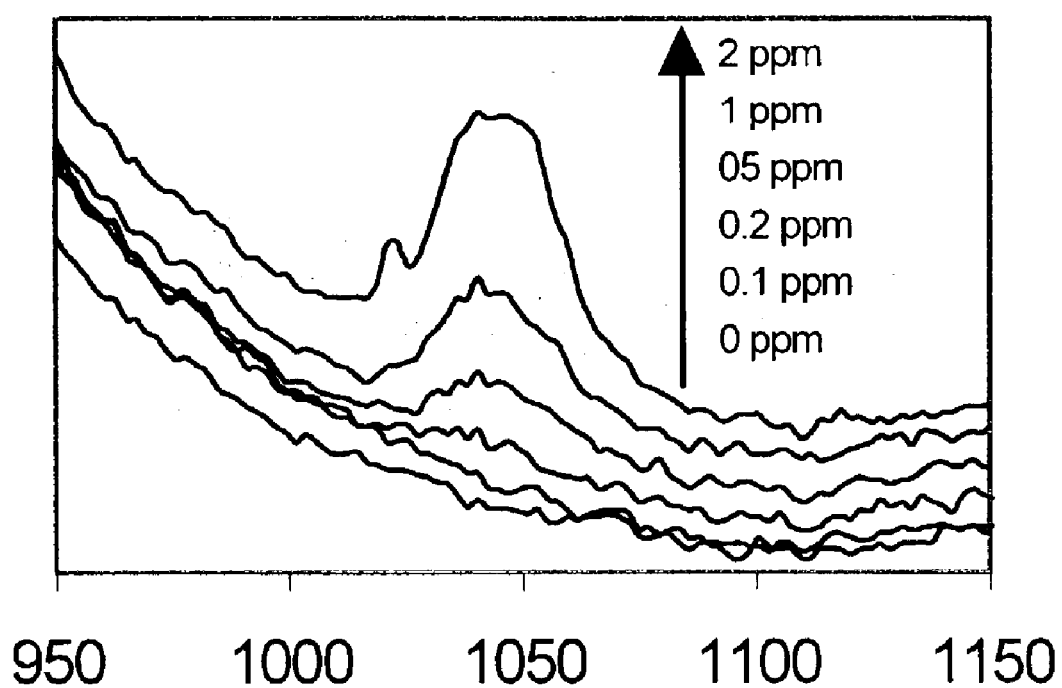
FIG. 7A is a enlarge view of a portion of FIG. 7.

In order to determine the lowest nitrate/nitrite concentration that could be detected by UV resonance Raman spectroscopy, measurements were performed of Raman spectra as a function of nitrate/nitrite concentration in pure water. FIGS. 6 and 7 show spectra of $NO_2^-$ and $NO_3^-$ respectively.

Figure 8:
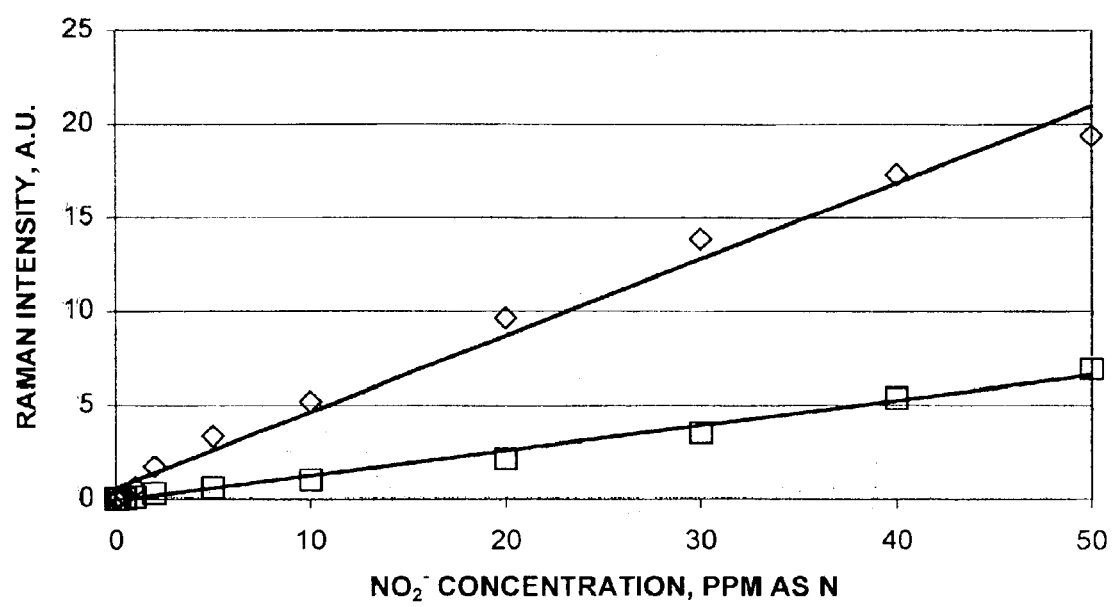
FIG. 8 depicts the dependence of the $NO_2$ Raman band intensity on nitrite concentrations.
Figure 8A:
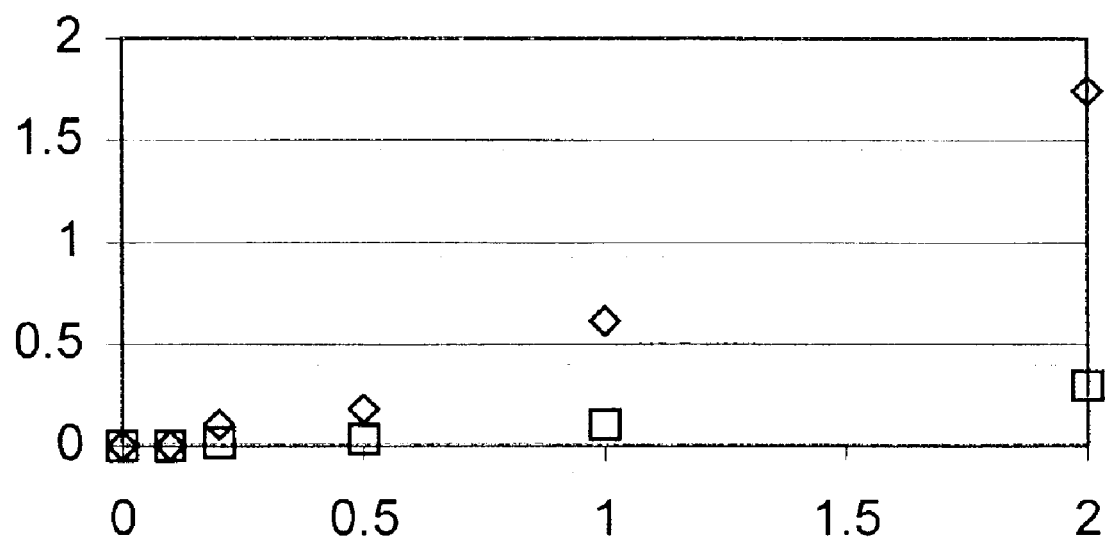
FIG. 8A is an enlarge view of a portion FIG. 8.
Figure 9:
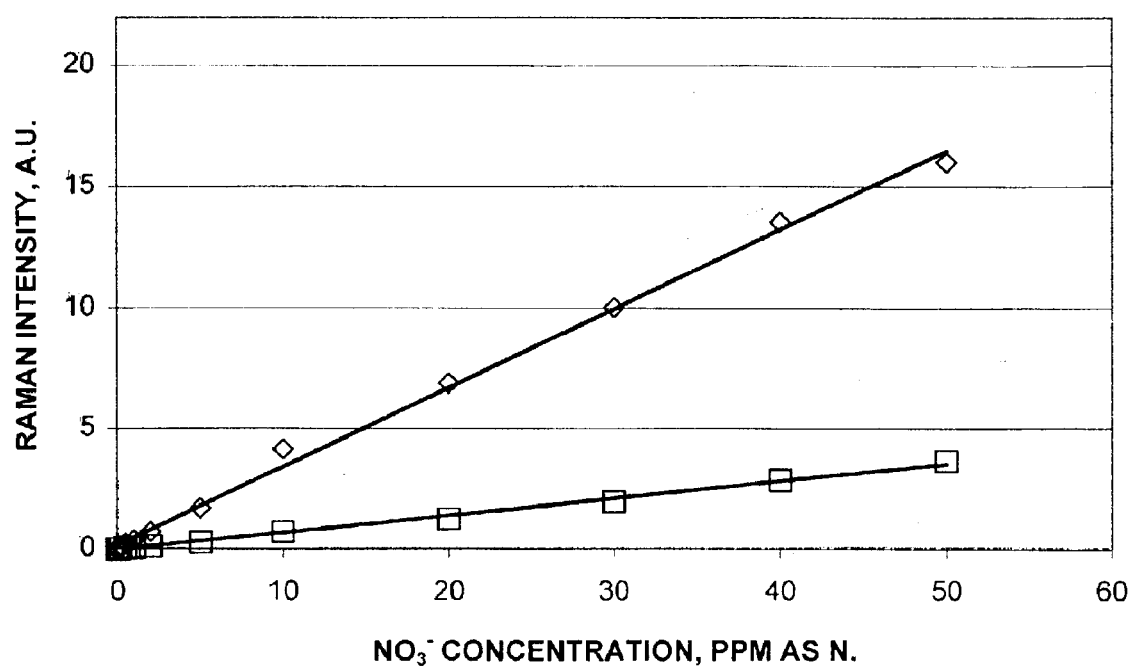
FIG. 9 depicts the dependence of the $NO_3$ Raman band intensity on nitrate concentrations.
Figure 9A:
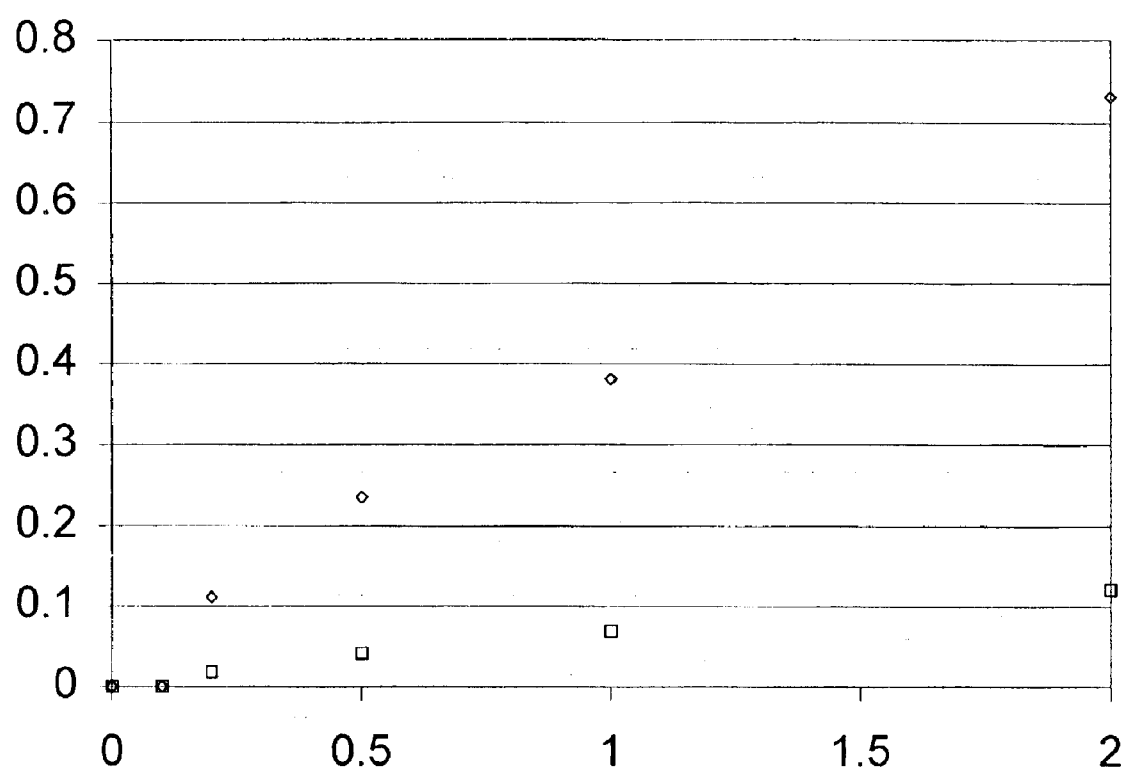
FIG. 9A is an enlarge view of a portion FIG. 9.

On FIGS. 8 and 9 dependencies of the relative intensities for both nitrate and nitrite as a function of analyte concentration are presented. These figures show a quite linear intensity dependence of the main Raman spectral features on the analyte concentration in the range 0.1 to 50 ppm.

Figure 10:
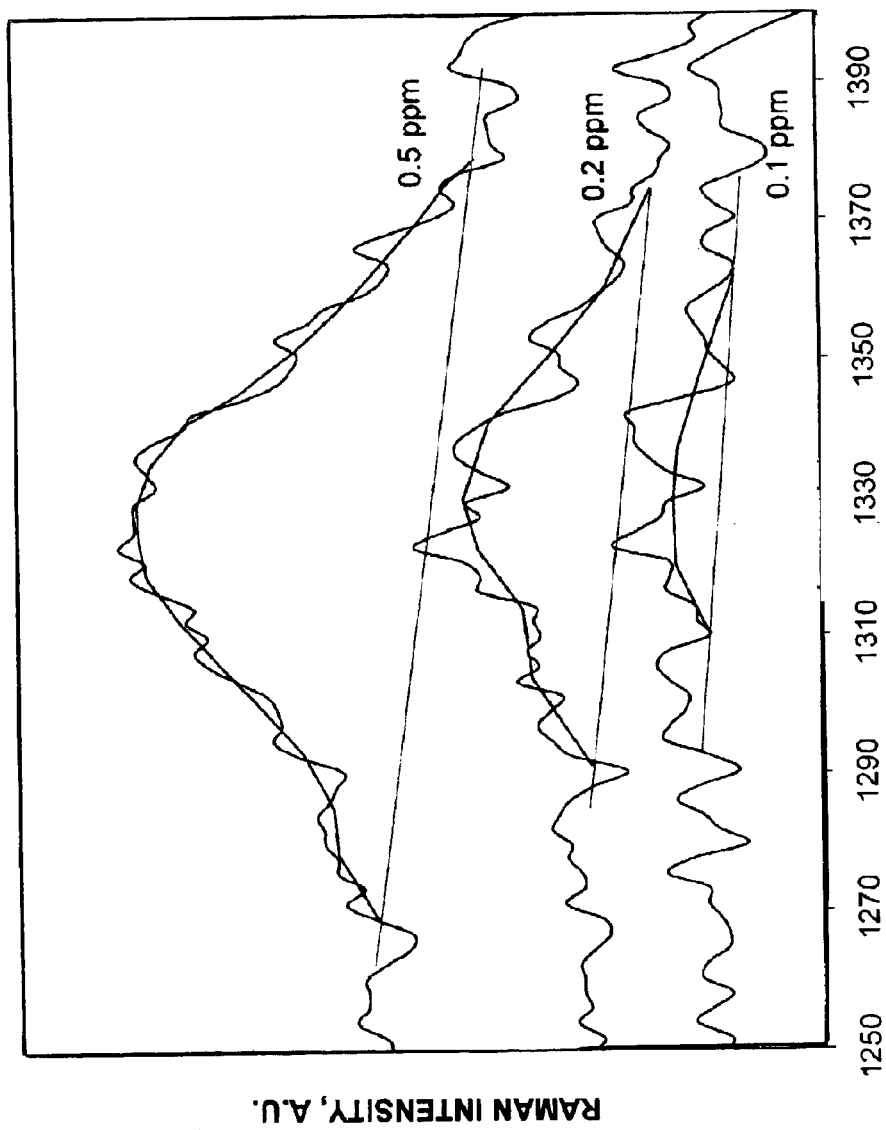
FIG. 10 depicts the determination of the detection limit for $NO_2$ in pure water.
Figure 11:
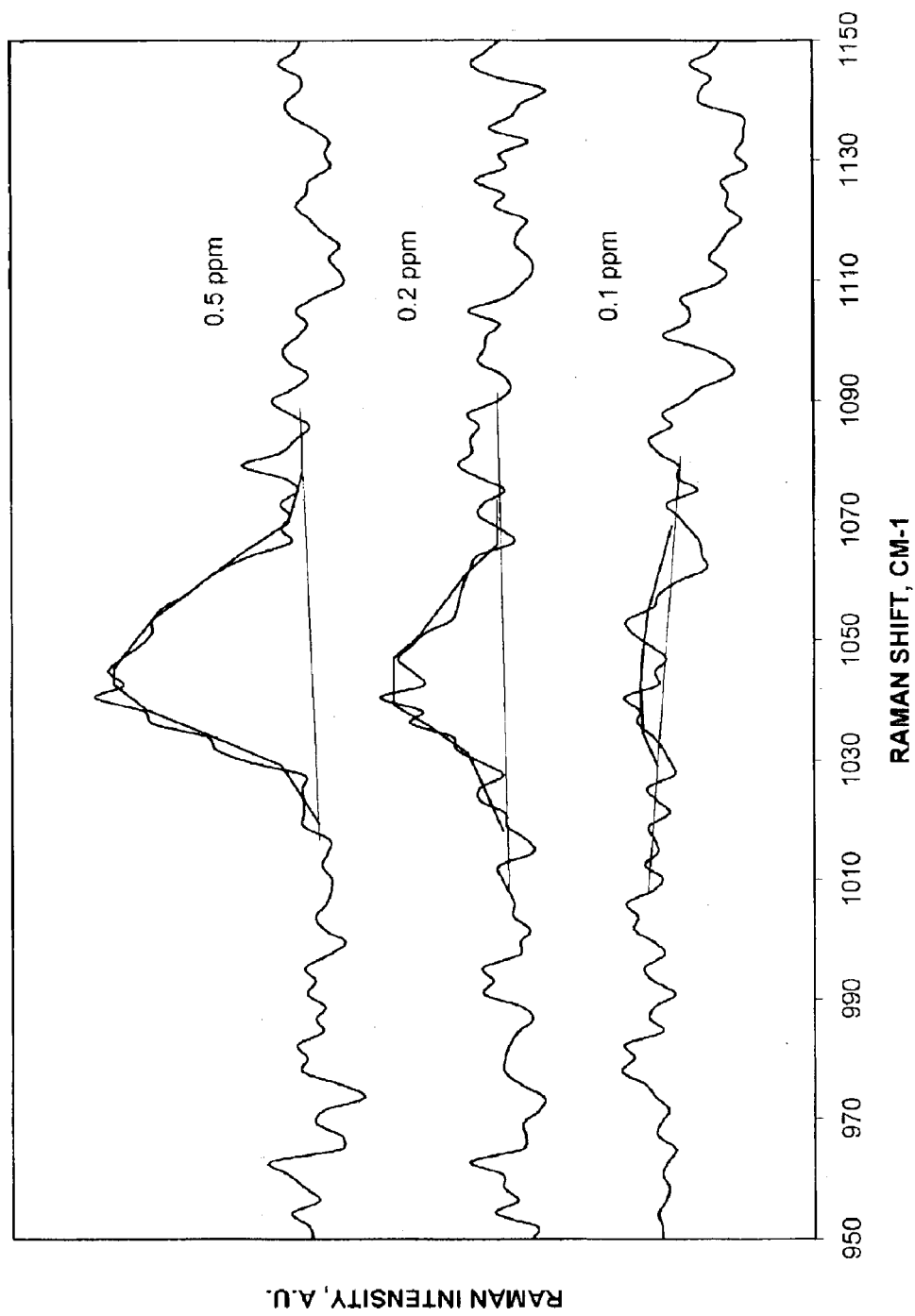
FIG. 11 depicts the determination of the detection limit for $NO_3$ in pure water.

To determine the detection limit for the measurements of the nitrate/nitrite concentrations using UV resonance Raman spectroscopy, the spectra were analyzed at the lowest concentrations measured: 0.5, 0.2, and 0.1 ppm. FIGS. 10 and 11 show the lowest concentration spectra for nitrite and nitrate in pure water. The Raman signal decreases as the concentration of analyte decreases. Raman spectra could be clearly observed for analyte concentrations as low as 0.2 ppm. At 0.1 ppm the Raman signal is almost undetectable because of the noise. Therefore, the detection limit for nitrate and nitrite is believed to be on the order of 0.2 ppm or below.

The Raman spectra were detected using a multichannel intensified CCD detector. Thus, the concentration of an analyte is obtained by taking the ratio of the analyte Raman band intensity relative to that of water. The noise observed within each individual spectrum is the dominant factor which determines both the detection limit and the concentration relative standard deviation. Since all laser intensity fluctuations are averaged out by using the relative intensity measurement, concentration standard deviations determined from replicate spectra will show similar relative standard deviations to those observed within individual spectra.

Figure 12:
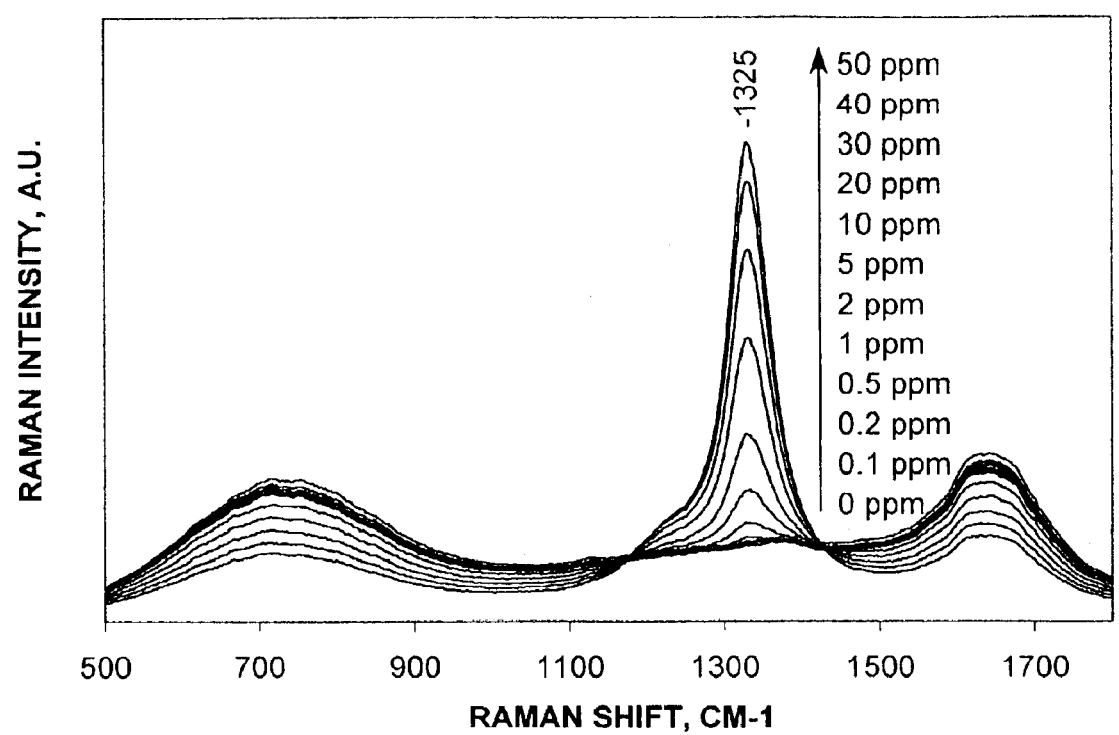
FIG. 12 depicts UV resonance of Raman spectra of $NO_2$ in filtered activated sludge wastewater as a function of $NO_2$ concentration.
Figure 13:
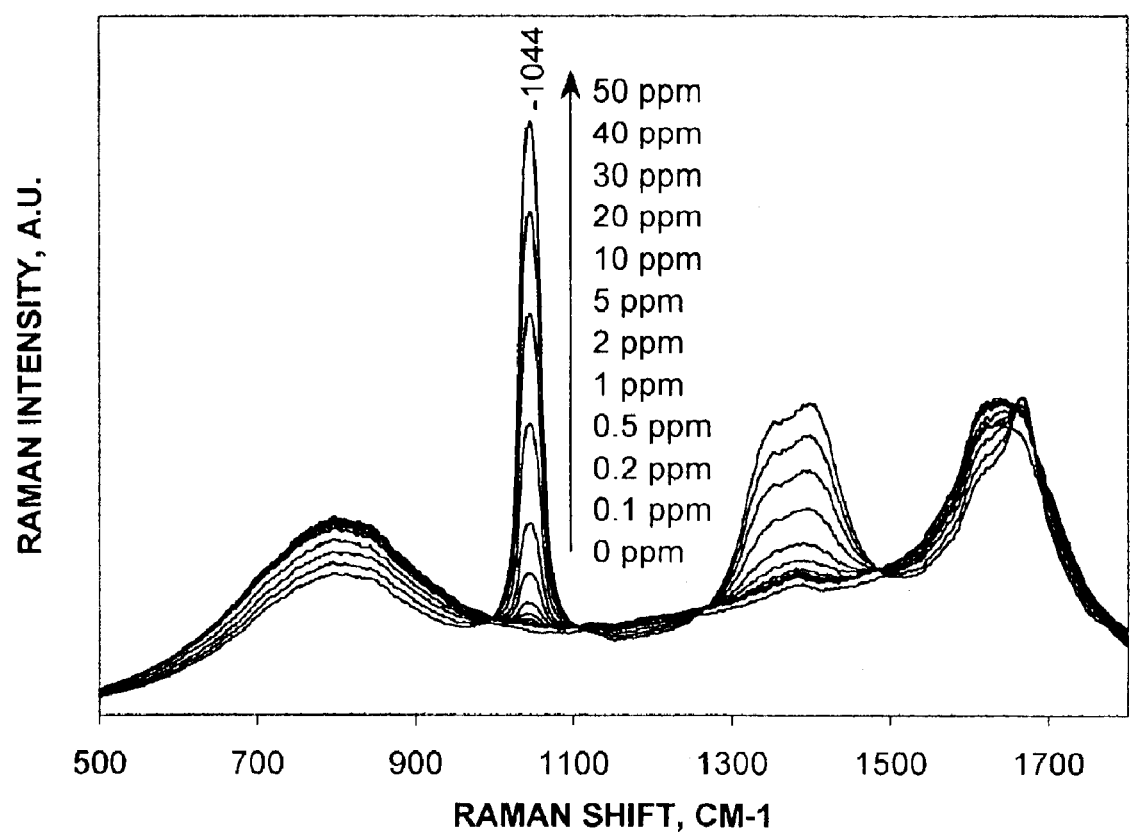
FIG. 13 depicts UV resonance of Raman spectra of $NO_3$ in filtered activated sludge wastewater as a function of $NO_3$ concentration.

FIGS. 12 and 13 show the UV resonance Raman spectra of $NO_2^-$ and $NO_3^-$ as a function of concentration in filtered activated sludge wastewater samples. As can be seen in these figures, the spectra of the filtered activated sludge wastewater do not show any significant differences from the spectrum of pure water. (Note that reference to wastewater samples in the context of the Raman spectral measurements are intended to refer to the filtered activated sludge wastewater samples which were prepared as described herein.)

Figure 14:
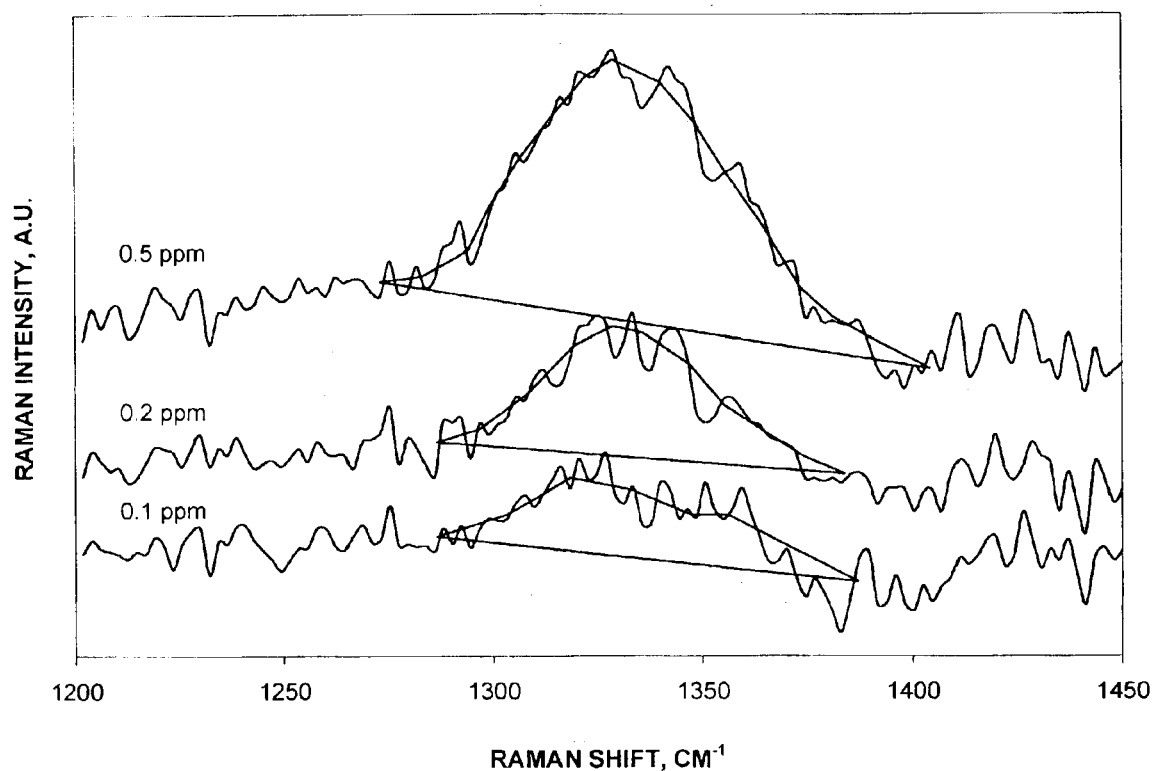
FIG. 14 depicts the determination of the detection limit for $NO_2$ in filtered activated sludge wastewater.
Figure 15:
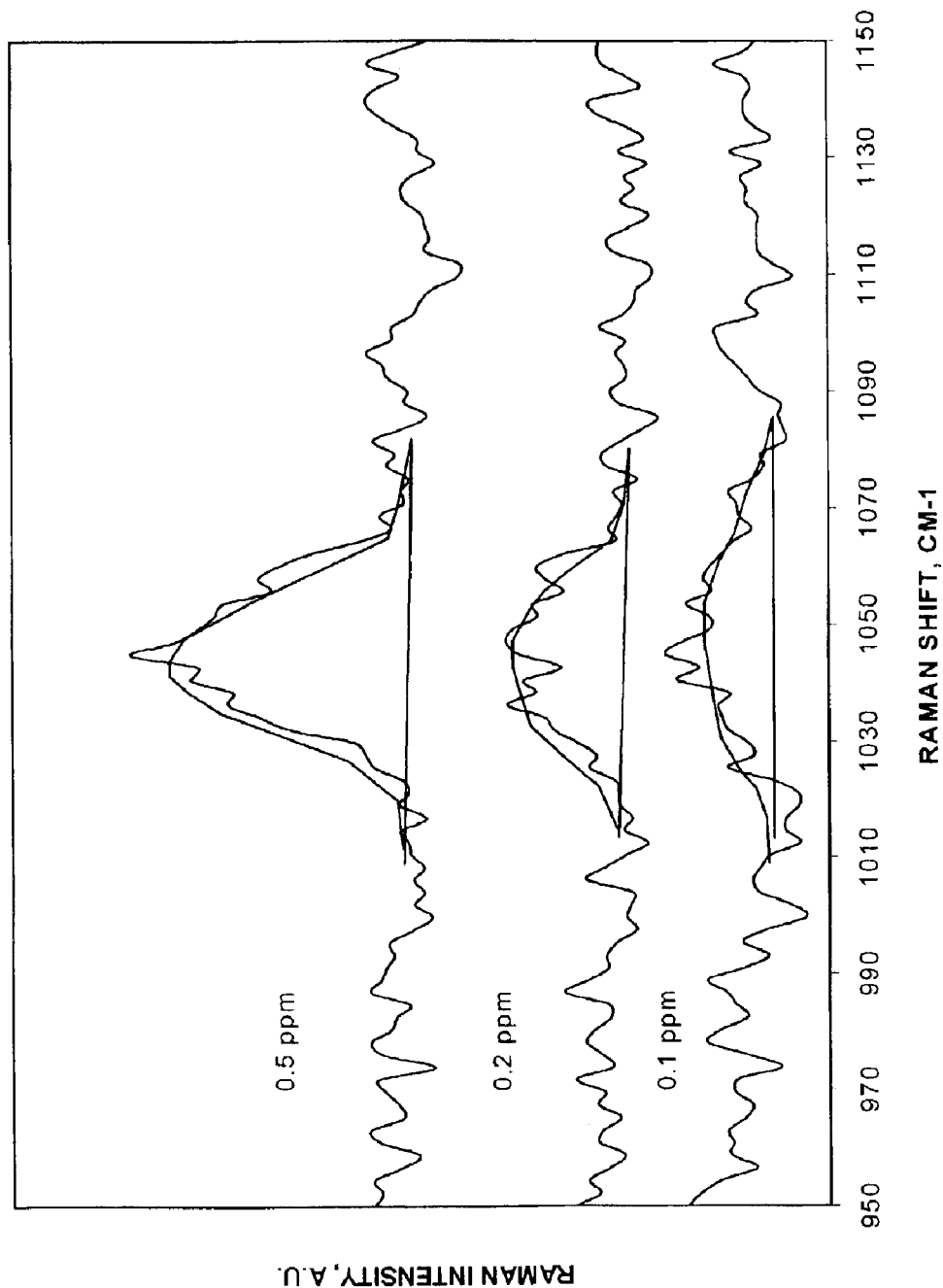
FIG. 15 depicts the determination of the detection limit for $NO_3$ in wastewater.

FIGS. 14 and 15 show the lowest concentration spectra for nitrite and nitrate in wastewater. The Raman signal decreases as the concentration of analyte decreases. Raman spectrum could be clearly observed for the analyte concentrations as low as 0.2 ppm. At 0.1 ppm the Raman signal is almost undetectable because of the noise.

Figure 16:
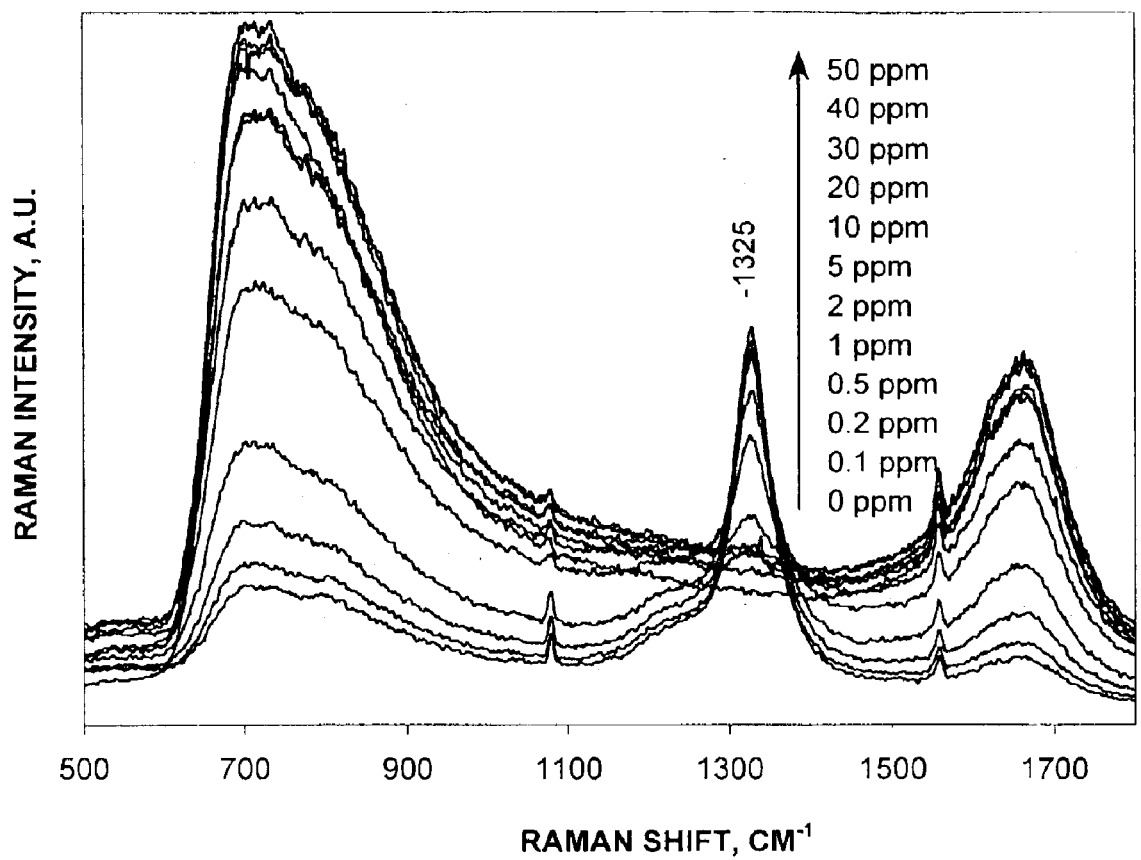
FIG. 16 depicts UV resonance spectra of $NO_2$ in pure water.
Figure 17:
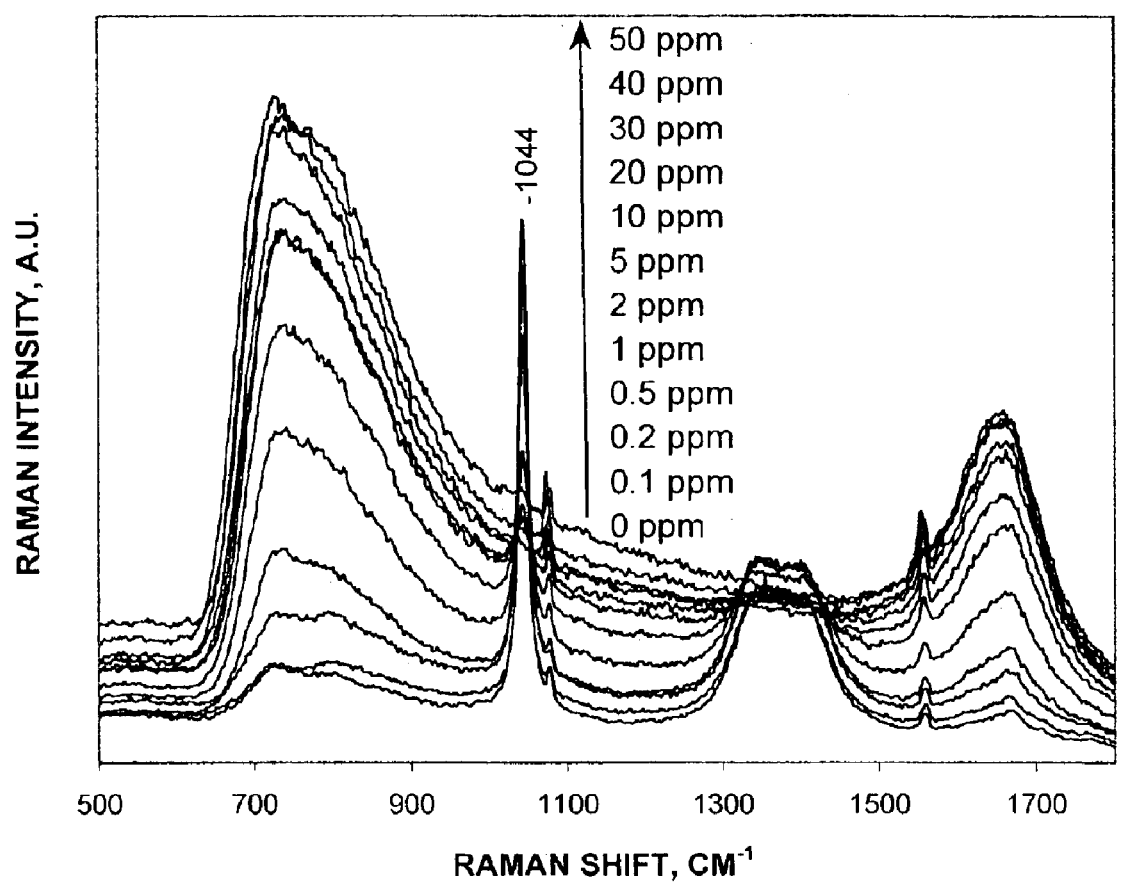
FIG. 17 depicts UV resonance Raman spectra of $NO_3$ in pure water.

It is important to use the optimal excitation wavelength in order to achieve the lowest detection limits. Therefore, 204 nm excitation wavelength was compared to 229 nm excitation. FIGS. 16 and 17 show 204 nm excited spectra of $NO_2^-$ and $NO_3^-$. The Raman spectra are essentially identical to that of 229 nm excitation.

Figure 18:
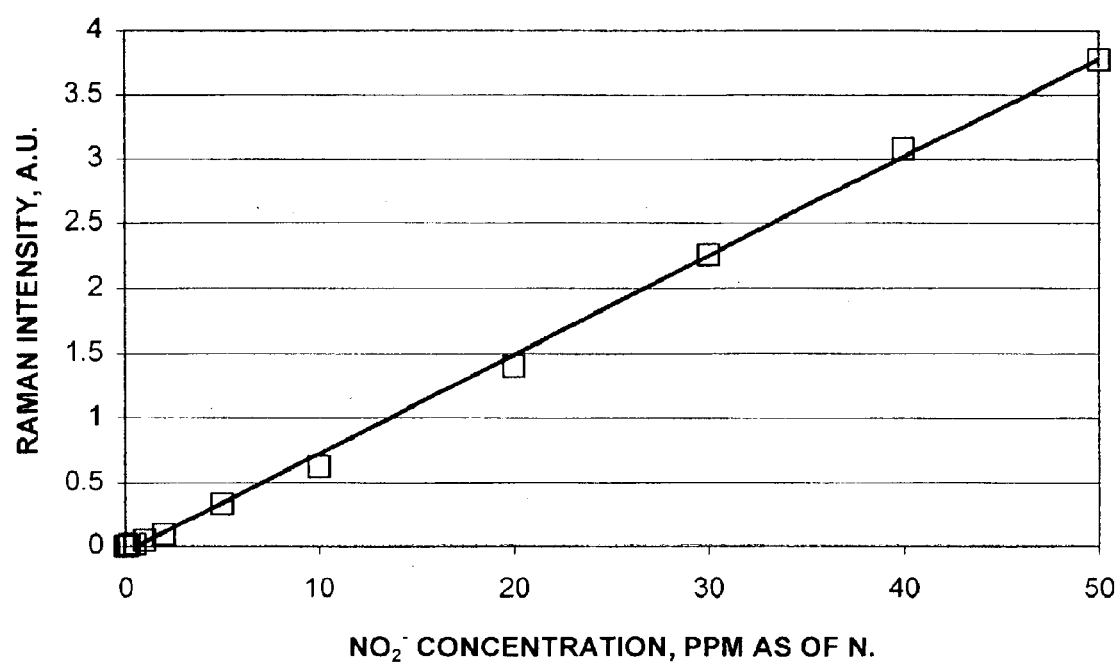
FIG. 18 depicts the dependence of $NO_2$ Raman band intensity in pure water.
Figure 19:
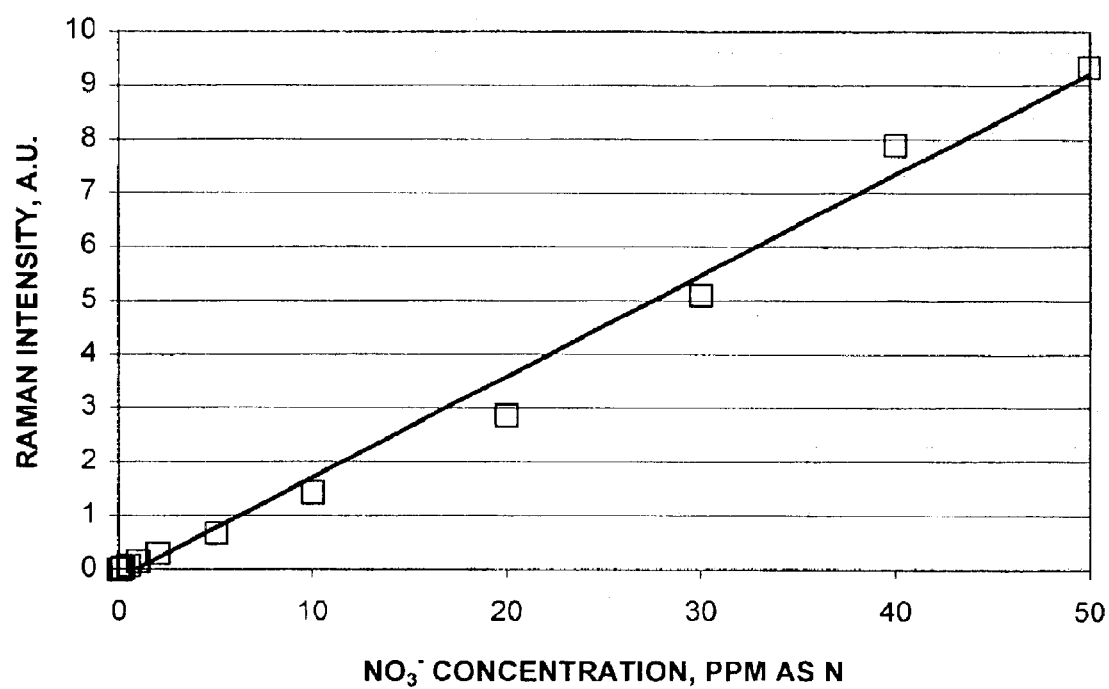
FIG. 19 depicts the dependency of $NO_3$ Raman band intensity on the concentration of nitrate.

The absolute intensities of the 1325 cm$^{-1}$ (FIG. 16) and 1044 cm$^{-1}$ (FIG. 17) bands increase with the concentration in the concentration range 0.1 to 5 ppm and become almost unchanged at higher concentrations due to spectral self-absorption. The water bands also lose their intensity due to the self-absorption. However, the ratio of the nitrate/nitrite signal to water signal increases linearly with concentration (FIGS. 18 and 19).

Self-absorption occurs when the excitation and Raman scattering wavelengths are within the absorption band. As a result, the exciting light and the Raman scattering light are strongly absorbed.

TABLE 1

Relative intensities of the $NO_2^-$ and $NO_3^-$ Raman bands at 10 ppm concentration.

| Excitation wavelength, nm | $NO_2^-$:I(1325)/I(1640) | $NO_3^-$:I(1044)/I(1640) |
|---|---|---|
| 204 | 0.6 | 1.44 |
| 229 | 0.7 | 0.72 |

Comparison of the relative Raman intensities of $NO_2^-$ and $NO_3^-$ with respect to internal (water band) intensity standard for 204 nm (FIGS. 18 and 19,—(□) symbol data points) and 229 nm (FIGS. 8 and 9,—(□) symbol data points) excitation shows that $NO_2^-$ Raman signal relative intensity does not increase when 204 nm versus 229 nm is used (Table 1). At the same time an approximate 2-fold increase is observed in the intensity of $NO_3^-$ Raman signal (Table 1). Thus, excitation 204 nm is preferable for nitrate detection. However, there is no advantage in using 204 nm instead of 229 nm excitation for detection of nitrite.

The three additional samples of filtered mixed liquor from extended aeration activated sludge treatment plants were analyzed with the Raman spectrometer using the 229 nm excitation wavelength. Sample 1 was a second sample from the Grand Coulee WWTP from which the filtered mixed liquor wastewater standard solutions for nitrate and nitrite were prepared. As in the earlier experiments the constituents in this sample showed no interference in the region of the Raman shifts for nitrate and nitrite. Also, as had been observed earlier, the levels of nitrate and nitrite in this second sample were below detection limits (less that 0.2 mg/l). Sample 2 was a mixed liquor filtrate from the Bingen, Wash. activated sludge treatment plant and the Raman spectral results were similar to those from Grand Coulee with no interferences and no detectable nitrate or nitrite.

The third sample was from the Zillah, WA WWTP which was experiencing a mild process upset with a more turbid effluent than normal at the time the sample was collected. The upset conditions had begun about two weeks previously. Because of the timing of the sample collection it was not possible to collect a sample which was fully depleted of nitrate and nitrite. In lieu of reaching the depletion end point, the filtered sample was analyzed for $NO_X$ using the Hach cadmium reduction method which is usually a good approximation for nitrate. The result of this analysis was 4 ppm.

Figure 20:
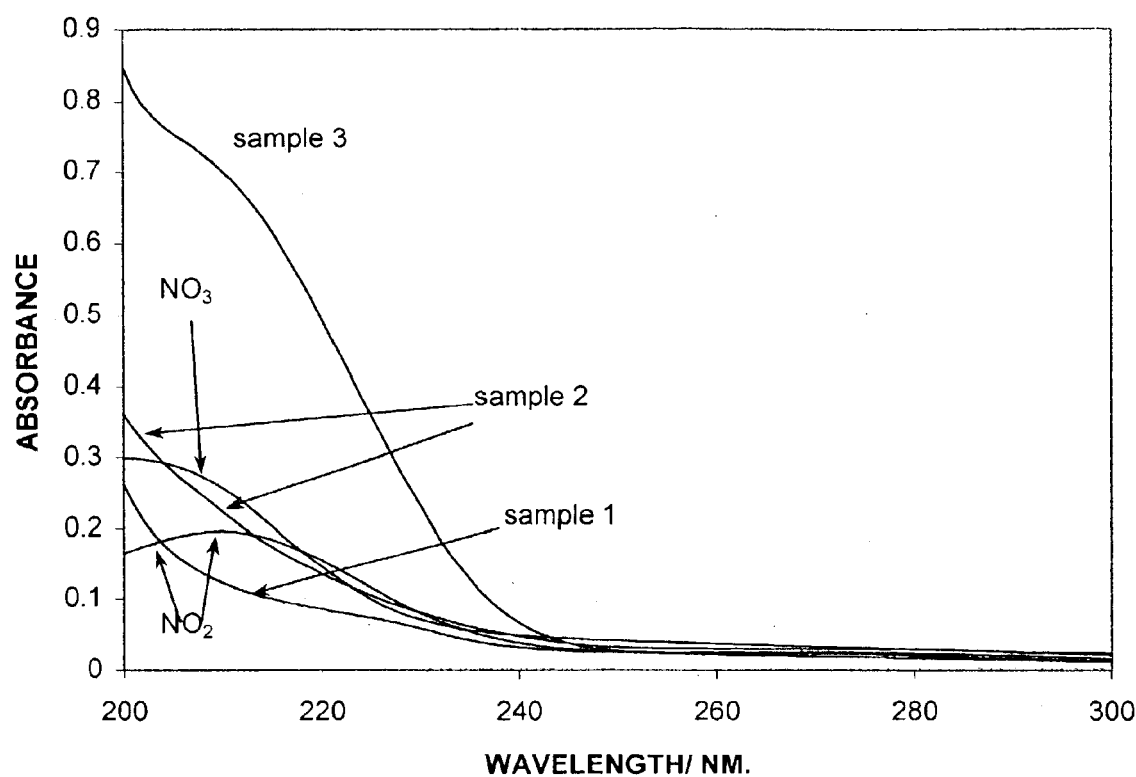
FIG. 20 depicts UV absorption spectra of nitrite and nitrate in pure water.

FIG. 20 shows the UV-visible absorption spectra for the three filtered wastewater samples as well as those for 1.0 ppm nitrate and nitrite standard solutions in pure water. As can be seen in this figure, Sample 3 from the Zillah plant shows significantly more absorption in the 200 to 240 nm range than do the other samples. This is consistent with the fact that Sample 3 contained 4 ppm $NO_X$ and more turbidity than the other samples.

Figure 21:
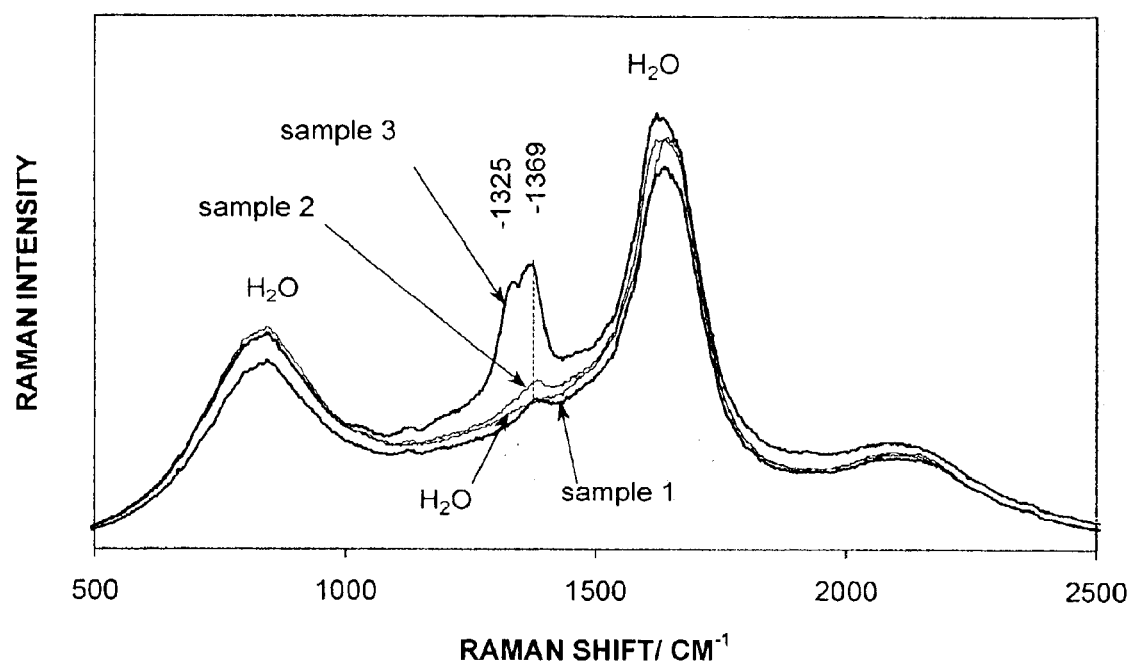
FIG. 21 depicts UV resonance Raman spectra of pure water and filtered activated sludge wastewater.
Figure 22:
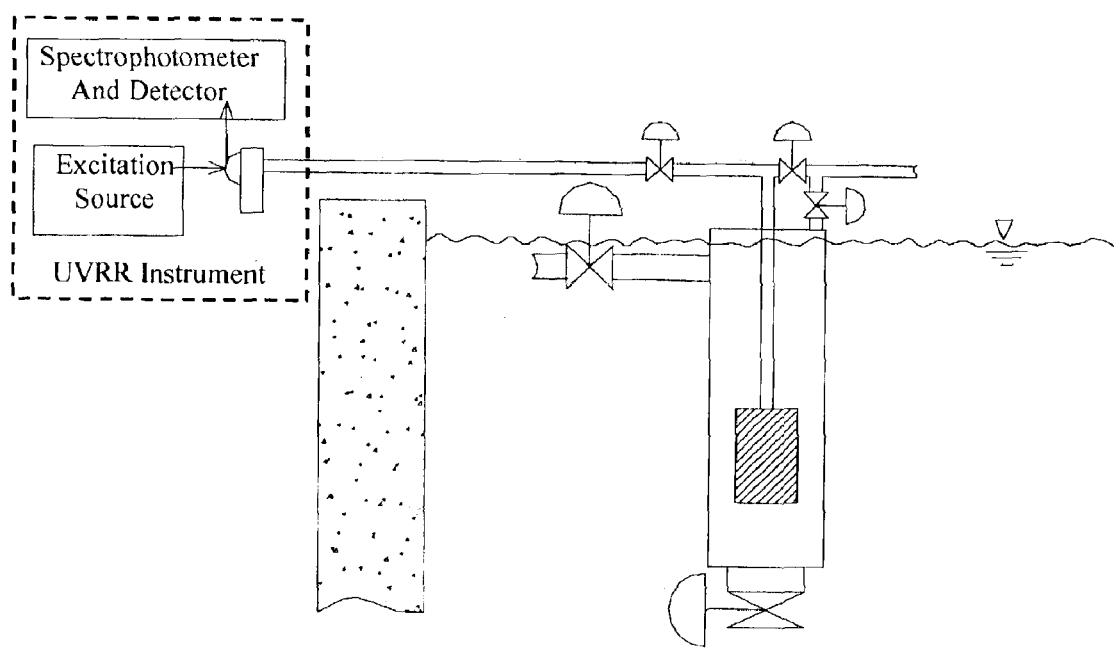
FIG. 22 is a schematic diagram of a UVRR monitoring system.

FIG. 21 shows the Raman spectra at 229 nm excitation for each of these three filtered activated sludge wastewater samples as well as that of pure water. Raman spectra of the samples 1 and 2 are not very different from the spectrum of pure water. The only spectral feature observed is a minor band at 1369 cm$^{-1}$. This band does not interfere with the nitrite Raman band since the spectral interval between those two bands is approximately 45 cm$^{-1}$ which is larger than the nitrite 1325 cm$^{-1}$ Raman band halfwidth. It can be concluded from this that the Raman spectrum of a filtered activated sludge mixed liquor wastewater is typically very similar to that of pure water and relatively independent of the specific WWTP location provided that the plant is functioning properly.

The Raman spectra for Sample 3 from the Zillah plant, however, is significantly different from the others. This sample shows major spectral bands at both 1325 cm$^{-1}$ and 1369 cm$^{-1}$ and no band at all at 1044 cm$^{-1}$. This indicates that this sample contained no nitrate and that, in fact, all of the $NO_X$ measured by the cadmium reduction method was actually nitrite. In retrospect this result can be explained by the upset conditions at the treatment plant in which the *nitrobacter* group of bacteria had been lost from the system. This result is a very graphic example of the power of an analytical tool which can simultaneously measure nitrate and nitrite down to very low detection levels to provide both process control variable input and diagnostic capabilities for plant upset conditions.

The important points that are demonstrated in the UV resonance Raman investigations as discussed above can be summarized as follows:

1. The UV resonance Raman spectra of nitrite and nitrate are distinct, and main spectral features are well separated;
2. UV resonance Raman spectroscopy enables detection of nitrate and nitrite in the concentration range from 0.2 to 50 ppm.
3. The UV resonance Raman spectra of $NO_2^-$ and $NO_3^-$ in filtered activated sludge wastewaters have the same detection limits as in pure water.
4. The Raman excitation wavelength for measuring $NO_2^-$ and $NO_3^-$ can be anywhere within the range of 200 to 240 nm.

In order to measure the nitrate and nitrite concentrations in an activated sludge reactor using UV resonance Raman spectroscopy it is necessary to first filter the mixed liquor to be analyzed. Without filtration the bacterial floc particles would scatter light and very significantly reduce the signal to noise ratio, and therefore, the detection limits that could be obtained. Filtration of the sample stream could be continuous or semi-continuous since a finite time period is required to make each Raman measurement. Preferably, the solids content of the sample to be analyzed is 10 ppm or less, more preferably in the range of 0.5 to 10 ppm.

Depending on the power of the excitation source, the desired detection limits and other factors, the accumulation time for a single measurement could range from 30 seconds to 10 minutes or more. Semi-continuous measurement strategies could also be employed in which the sampling interval was short relative to the optimal accumulation time and the measured value of the analyte continuously updated (e.g.

once every 5 seconds) using a software algorithm. The algorithm would use the sampling rate as well as the rate of accumulation of photons measured at the detector to calculate the concentration of the analyte corresponding to a specific Raman band. In this way a continuous real time output could be closely approximated. However, in the application of this monitoring method to BNR processes the rates of change of nitrate and nitrite concentration in a reactor will be relatively slow in relation to a time interval of 5 to 10 minutes and process variable measurements occurring at similar intervals should be sufficient for process control.

In developing an in situ filtration assembly for this application the following were established as important performance criteria:

1. Effective removal of particulate solids which would scatter light.
2. The ability to reliably deliver a filtrate stream continuously or semi-continuously without excessive maintenance requirements.
3. The ability to produce a filtrate that is representative of the dissolved constituents of the mixed liquor. To achieve this performance criterium the filtrate must not undergo biologically induced transformation as might result from filtering a sample under conditions where significant amounts of active biomass has accumulated on or within the filter media.

The first approach investigated for achieving these criteria utilized a cross-flow filtration assembly. The objective of this approach was to minimize the build-up of biomass on the filtration media by the scouring action of the cross-flow hydraulic configuration. It was also intended that the flow rate through the media would be maintained at a high enough level to minimize the potential for biological conversions of nitrogen species by bacteria as the filtrate passes through the media. Using the PolyCap AS 0.45 $\mu$m filter capsule in this configuration, the diaphragm metering pump was set to draw approximately 240 ml/min through the media. In these tests the flow rates through the filter dropped off to approximately 120 ml/min after only one minute. Backflushing with air at one minute intervals would not restore the initial flow rates of 240 ml/min. These flux rates were significantly higher than what are believed would be required to minimize biological transformations within the media, and therefore, we thought that it should be possible to increase the intervals between backflushing by reducing the pumping rates. However, it was not possible to turn down the flow rate further using the diaphragm metering pump, even though the pump was theoretically rated to deliver as little as 20 ml/min. As headloss across the filter increased or when further turn down of the pump was attempted, it appeared that cavitation or air binding was occurring. Under these conditions the pumping rate would become erratic and eventually stop altogether.

Pleated cellulose and pleated polyester cartridges of 2 $\mu$m and 1 $\mu$m pore size, respectively, were also tested using the cross flow filtration assembly with similar results. Flow rates dropped off quickly and the pump performance became erratic making it difficult to reliably measure the flux rates. The problem was compounded by the fact that the pleated filter cartridges tended to collapse as the headloss across the media increased. Air backflushing was also a problem with these cartridges since it was not possible to obtain uniform air distribution at low air flow rates and higher flow rates caused the media to rupture at a seam.

In an effort to improve the performance of the in situ filtration system, a new assembly was constructed which could be operated using only compressed air and valves.

Compressed air is used to pressurize a filtration chamber housing a PolyCap AS 0.45 $\mu$m cartridge. The PolyCap AS was chosen because it can withstand high differential pressures and the absolute nylon membrane created enough back pressure that uniform backflusing with air is possible. Since a Raman spectral measurement can be performed semi-continuously on a very small sample volume (10 to 20 ml), the sampling portion of a filtration cycle can be of short duration with the remainder of the cycle is used for backflushing with air. The backflushing action not only cleans the media, but also prevents liquid from passing through the membrane during this period thus minimizing the potential for biological fouling. For example, if a 20 ml sample could be drawn in 20 seconds and the cycle time is set at 5 minutes, then backflushing would be taking place for 4 minutes and forty seconds or 93% of the cycle. If more frequent sampling was required for an application then the cycle time could be shortened or multiple cartridges could be used in a staggered configuration.

The bench scale pressure chamber filtration assembly was tested through repeating 5 minute cycles over a two hour period. During the sampling portion of each cycle the chamber was pressurized to 20 psi and the time required to draw a 20 ml sample aliquot was recorded. Mixed liquor activated sludge from two different municipal WWTPs were tested. The first suspension tested had a mixed liquor suspended solids concentration of 6000 mg/L and the average time required to draw a 20 ml sample was 18 seconds. This sampling time remained relatively constant throughout the test with no apparent increase over time (i.e., no decline in flux rate through the membrane). The second suspension tested had a more typical mixed liquor suspended solids level of 3000 mg/L, and the average time required to draw a 20 ml sample was 11 seconds. This observed flux rate through the membrane with the second mixed liquor sample also remained relatively constant throughout the test and if anything tended to increase slightly as the test progressed.

These initial investigations using the pressurized in situ filtration assembly were very encouraging and suggest that the sample conditioning necessary for the Raman spectral measurements can be readily achieved using a relatively simple system requiring no pumps. The bench scale assembly utilized manual valves to control the sampling and backwash cycles. The assembly could be automated with electric or air operated valves together with a small programmable controller to provide for unattended operation.

Long term control of membrane fouling using a similar air backwash method was shown by Choo and Stensel, (1999) in a year long continuous investigation using a PolyCap AS membrane cartridge. In this research the membrane cartridge was installed in a lab scale sequencing batch reactor which was operated to achieve simultaneous nitrification and denitrification. As with the second filtration assembly, pressurization of the reactor compartment was used to force filtrate through the membrane. This supports the experience that pressurization is a more reliable and effective method than a mechanical pump for the design of the in situ filtration element to be used in our proposed monitoring system.

The present invention may also be employed to assist in the control of the removal of ammonia under conditions as depicted in the two step process as follows:

$$2NH_4^+ + 3O_2 \rightarrow 2NO_2^- + 4H^+ + 2H_2O \quad \text{Equation 7}$$

$$2NH_4^+ + 2NO_2^- \rightarrow 2N_2 + 4H_2O \quad \text{Equation 8}$$

With the overall reaction being:

$$4NH_4^+ + 3O_2 \rightarrow 2N_2 + 6H_2O + 4H^+ \quad \text{Equation 9}$$

More particularly, in the method for the removal of ammonium ions from an aqueous sample by contact of said ammonium ions with oxygen to yield nitrogen, water and hydrogen ions according to the above Equations 7, 8 and 9, the improvement wherein the level of oxygen present as a reactant is determined by determining the ratio of $NO_3^-$ to $NO_2^-$ present in the sample by subjecting the sample to ultraviolet resonance Raman spectroscopy within the range of wavelengths of 200–240 nm, and thereby determining the quantity of $NO_3^-$ and $NO_2^-$ present in the sample based on said Raman spectral measurement, and subsequently controlling the amount of oxygen contacting said ammonium ions based on said measurement whereby nitrate ion formation is minimized.

With respect to Equation 7, it is necessary to avoid the presence of dissolved oxygen (DO) in amounts such that nitrate ions are formed instead of nitrite ions, as nitrate ions will not participate in Equation 8 (and hence will accumulate in the system). However, it is difficult to measure with any accuracy levels of DO to enable the process to be adequately regulated. Also, as discussed above, the DO levels also are not accurate predictors of the level of nitrite/nitrate present. The use of the present invention is thus found to be highly advantageous in the determination of the amount of nitrite/nitrate levels in the sample, which levels can be correlated the amount of oxygen required in the system to provide the necessary reaction with the ammonium ions while avoiding the undesirable formation of nitrate ions. By way of further advantage, by use of appropriate algorithm(s), the desired monitoring of the process and oxygen control can occur substantially simultaneously with the determination of the nitrite/nitrate ions present in the sample.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the determination of $NO_2^-$ and $NO_3^-$ in an activated sludge wastewater treatment reactor comprising subjecting an aqueous portion of said activated sludge wastewater to ultraviolet resonance Raman spectroscopy within the range of wavelengths of 200–240 nm, and determining the presence of $NO_2^-$ and $NO_3^-$ based on said Raman spectral measurement.

2. The method of claim 1, wherein solids present in said aqueous portion are removed so that said aqueous portion is substantially-free of suspended solids prior to determining the presence of $NO_2^-$ and $NO_3^-$ based on said Raman spectral measurement.

3. The method of claim 1, wherein said reactor is a biological nutrient removal (BNR) reactor.

4. The method of claim 1, wherein said aqueous portion is derived from filtered activated sludge wastewater.

5. The method of claim 1, wherein said aqueous portion has a solids content of 10 ppm or less.

6. In a method for the removal of ammonium ions from an aqueous sample by contact of said ammonium ions with oxygen the improvement comprising determining the ratio of $NO_3^-$ to $NO_2^-$ present in said sample by subjecting said sample to ultraviolet resonance Raman spectroscopy within the range of wavelengths of 200–240 nm, and thereby determining the quantity of $NO_3^-$ and $NO_2^-$ present in said sample based on said Raman spectral measurement, and controlling the amount of oxygen contacting said ammonium ions based on said determined ratio of $NO_3^-$ to $NO_2^-$.

7. The method of claim 6, wherein said aqueous sample is derived from a wastewater treatment reactor.

8. The method of claim 7, wherein said reactor is a biological nutrient removal (BNR) reactor.

9. The method of claim 6, wherein said aqueous sample is derived from filtered activated sludge wastewater.

10. The method of claim 9, wherein said aqueous sample has a solids content of 10 ppm or less.

11. The method of claim 6, wherein said contact of said ammonium ions with oxygen yields nitrogen, water and hydrogen ions according to the equation $4NH_4^+ + 3O_2 \rightarrow 2N_2 + 6H_2O + 4H^+$ and wherein nitrate ion formation is minimized.

12. The method of claim 6, wherein said contact of said ammonium ions with oxygen yields nitrogen, water and hydrogen ions by simultaneous nitrification and denitrification (SNdN) according to the equations $NH_4^+ + 2O_2 \rightarrow NO_3^- + H_2O + 2H^+$ and $NO_3^- \rightarrow NO_2^- \rightarrow NO \rightarrow N_2O \rightarrow N_2$ and whereby dissolved oxygen (DO) levels are maintained as low as possible without losing nitrification.

13. The method of claim 11, wherein said aqueous sample is derived from wastewater treatment reactor.

14. The method of claim 13, wherein said reactor is a biological nutrient removal (BNR) reactor.

15. The method of claim 11, wherein said aqueous sample is derived from filtered activated sludge wastewater.

16. The method of claim 15, wherein said aqueous sample has a solids content of 10 ppm or less.

17. The method of claim 12, wherein said aqueous sample is derived from a wastewater treatment reactor.

18. The method of claim 17, wherein said reactor is a biological nutrient removal (BNR) reactor.

19. The method of claim 12, wherein said aqueous sample is derived from filtered activated sludge wastewater.

20. The method of claim 19, wherein said aqueous sample has a solids content of 10 ppm or less.

* * * * *